US 10,273,225 B2

(12) United States Patent
Adams et al.

(10) Patent No.: US 10,273,225 B2
(45) Date of Patent: *Apr. 30, 2019

(54) PYRAZINES AS MODULATORS OF GPR6

(71) Applicant: Takeda Pharmaceutical Company Limited, Osaka (JP)

(72) Inventors: Mark E. Adams, San Diego, CA (US); Jason W. Brown, San Diego, CA (US); Stephen Hitchcock, San Diego, CA (US); Maria Hopkins, San Diego, CA (US); Shota Kikuchi, San Diego, CA (US); Betty Lam, San Diego, CA (US); Holger Monenschein, San Diego, CA (US); Holly Reichard, San Diego, CA (US); Huikai Sun, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/979,069

(22) Filed: May 14, 2018

(65) Prior Publication Data

US 2018/0258073 A1    Sep. 13, 2018

Related U.S. Application Data

(62) Division of application No. 15/118,461, filed as application No. PCT/US2015/015841 on Feb. 13, 2015, now Pat. No. 10,000,468.

(60) Provisional application No. 61/940,294, filed on Feb. 14, 2014.

(51) Int. Cl.
| C07D 401/04 | (2006.01) |
| C07D 401/14 | (2006.01) |
| C07D 241/26 | (2006.01) |
| C07D 241/28 | (2006.01) |
| A61K 31/497 | (2006.01) |
| A61K 31/506 | (2006.01) |
| A61K 31/551 | (2006.01) |

(52) U.S. Cl.
CPC .......... *C07D 401/14* (2013.01); *A61K 31/497* (2013.01); *A61K 31/506* (2013.01); *A61K 31/551* (2013.01); *C07D 241/26* (2013.01); *C07D 241/28* (2013.01); *C07D 401/04* (2013.01)

(58) Field of Classification Search
CPC ... C07D 401/14; C07D 401/04; C07D 241/28
See application file for complete search history.

(56) References Cited

U.S. PATENT DOCUMENTS

| 4,159,331 | A | 6/1979 | McCall | |
| 5,489,593 | A * | 2/1996 | Palmer | C07D 209/42 514/218 |
| 5,563,142 | A * | 10/1996 | Palmer | C07D 209/42 514/183 |
| 7,902,379 | B2 * | 3/2011 | Lubisch | C07D 401/12 548/466 |
| 8,129,534 | B2 | 3/2012 | Maienfisch | |
| 8,350,055 | B2 * | 1/2013 | Oost | C07D 401/12 548/466 |
| 8,580,842 | B2 * | 11/2013 | Lubisch | C07D 401/04 514/414 |
| 8,957,073 | B2 * | 2/2015 | Allen | C07D 401/14 514/235.8 |
| 9,045,422 | B2 | 6/2015 | Hitchcock | |
| 9,487,505 | B2 * | 11/2016 | Lubisch | C07D 401/04 |
| 9,487,526 | B2 | 11/2016 | Hitchcock et al. | |
| 9,718,803 | B2 * | 8/2017 | Allen | C07D 401/14 |
| 9,770,452 | B2 * | 9/2017 | Hitchcock | C07D 241/44 |
| 10,000,468 | B2 * | 6/2018 | Adams | C07D 401/04 |
| 2003/0055247 | A1 | 3/2003 | Cosford et al. | |
| 2005/0239800 | A1 | 10/2005 | Wang et al. | |
| 2006/0199828 | A1 | 9/2006 | Jaeschke et al. | |
| 2007/0149547 | A1 | 7/2007 | Bonnefous et al. | |

(Continued)

FOREIGN PATENT DOCUMENTS

| WO | 2001/060806 A2 | 8/2001 |
| WO | 2002/098864 A1 | 12/2002 |

(Continued)

OTHER PUBLICATIONS

CAS Abstract WO 2014028479 A1 (2014).*

(Continued)

*Primary Examiner* — Alexander R Pagano
(74) *Attorney, Agent, or Firm* — Matthew J. Russo; David M. Stemerick

(57) ABSTRACT

The present invention provides compounds of formula I:

I $$R_1 \diagdown Z \diagdown X_1 \diagdown ( )_s$$
$$(R_3)_p \diagdown X_2 \diagdown \begin{array}{c} N \\ \end{array} \diagdown (R_4)_r$$
$$R_2 \diagdown N$$

which are useful as modulators of GPR6, pharmaceutical compositions thereof, methods for treatment of conditions associated with GPR6, processes for making the compounds and intermediates thereof.

12 Claims, No Drawings

(56) References Cited

U.S. PATENT DOCUMENTS

2012/0184572 A1    7/2012  Song et al.
2017/0035775 A1    2/2017  Hitchchock et al.

FOREIGN PATENT DOCUMENTS

| WO | 2003/051366 A2 | 6/2003 | |
|----|----|----|----|
| WO | 2003/076422 A1 | 9/2003 | |
| WO | 2004/054617 A1 | 7/2004 | |
| WO | 2005/011657 A2 | 2/2005 | |
| WO | 2005/079802 A1 | 9/2005 | |
| WO | 2006/124748 A2 | 11/2006 | |
| WO | 2007/044085 A2 | 4/2007 | |
| WO | 2010/008739 A2 | 1/2010 | |
| WO | 2011/139489 A2 | 11/2011 | |
| WO | 2011/143495 A1 | 11/2011 | |
| WO | 2014/028479 A1 | 2/2014 | |
| WO | WO-2014028479 A1 * | 2/2014 | ........... C07D 241/44 |
| WO | 2015/061247 A2 | 4/2015 | |

OTHER PUBLICATIONS

Lacivita, Enza, et al., "Selective Agents for Serotonin2C 5-HT2C Receptor", Current topics in Medicinal Chemistry, Bentham Science Publishers LTD., Hilversum; NL, vol. 6, No. 18, Jan. 1, 2006, pp. 1927-1970.
PCT, PCT/US2015/015841 "International Search Report", dated Apr. 30, 2015, 4 pages.

\* cited by examiner

PYRAZINES AS MODULATORS OF GPR6

CROSS-REFERENCE TO RELATED APPLICATIONS

This application is a divisional of U.S. application Ser. No. 15/118,461, filed Aug. 11, 2016, which is the U.S. National Stage entry under 35 U.S.C. § 371(c) of International Application PCT/US2015/015841, filed Feb. 13, 2015, which claims the benefit of U.S. Provisional Application No. 61/940,294, filed Feb. 14, 2014.

FIELD OF THE INVENTION

The present invention relates to medicinal chemistry, pharmacology, and medicine.

BACKGROUND OF THE INVENTION

The present invention provides compounds that are G-Protein-Coupled Receptor 6 (hereinafter referred to as GPR6) modulators. GPR6 is GPCR that signals via the Gs pathway. GPR6 receptors are highly expression in the central nervous system (CNS), particularly medium spiny neurons (MSNs) of the striatum, with minimal expression in peripheral tissues. The major striatal targets of dopaminergic innervation reside in the medium spiny neurons (MSNs) of the striatopallidal (indirect) and striatonigral (direct) output pathways. The MSNs of the direct output pathway express D1 dopamine receptors whereas those in the indirect pathway express D2 receptors. GPR6 is enriched in D2 receptor expressing MSNs in the striatum where GPR6 activity is functionally opposed to D2 receptor signaling. Antagonism or inverse agonism of Gs coupled GPR6 decreases cAMP in MSNs and provides a functional alternative to dopamine mediated activation of D2 receptors. Therefore, the compounds of the present invention are useful to treat a variety of neurological and psychiatric disorders, including Parkinson's disease.

SUMMARY OF THE INVENTION

The present invention provides a compound of formula I:

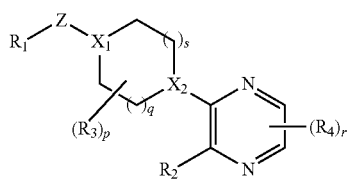

I wherein
$R_1$ is selected from the group consisting of optionally substituted $C_{3-8}$ cycloalkyl, optionally substituted $C_{3-6}$ heterocyclyl, optionally substituted $C_{6-10}$ aryl, and optionally substituted $C_{1-10}$ heteroaryl;
$X_1$ is N and $X_2$ is CH; or
$X_1$ is CH and $X_2$ is N; or
$X_1$ is N and $X_2$ is N;
when $X_1$ is N, Z is selected from the group consisting of $C_{1-6}$ alkylene, $C_{1-6}$ haloalkylene, —C(O)—, and —S(O)$_2$—;
when $X_1$ is CH, Z is selected from the group consisting of $C_{1-6}$ alkylene, $C_{1-6}$ haloalkylene, —O—, —C(O)—, —NH—, —S—, —S(O)—, and —S(O)$_2$—;
q is 0, 1, or 2;
s is 0, 1, or 2;
$R_2$ is —OR$_5$ or —NR$_6$R$_7$;
$R_3$, each time taken, is independently selected from the group consisting of $C_{1-6}$ alkyl, $C_{3-8}$ cycloalkyl, and trifluoromethyl;
p is 0, 1, or 2;
$R_4$, each time taken, is independently selected from the group consisting of optionally substituted $C_{1-6}$ alkyl, cyano, hydroxy, halo, optionally substituted $C_{3-6}$ heterocyclyl, —C(O)—R$_8$, —C(O)—N(R$_9$)(R$_{10}$), and —C(O)—OR$_{11}$;
r is 1 or 2;
$R_5$ is selected from the group consisting of $C_{1-6}$ alkyl and $C_{3-8}$ cycloalkyl;
$R_6$ is selected from the group consisting of hydrogen and $C_{1-6}$ alkyl;
$R_7$ is selected from the group consisting of optionally substituted $C_{1-6}$ alkyl, $C_{3-8}$ cycloalkyl, optionally substituted $C_{6-10}$ aryl, optionally substituted $C_{1-10}$ heteroaryl, and optionally substituted $C_{3-6}$ heterocyclyl;
$R_8$ is selected from the group consisting of hydrogen, optionally substituted $C_{1-6}$ alkyl, $C_{3-8}$ cycloalkyl, optionally substituted $C_{6-19}$ aryl, optionally substituted $C_{1-10}$ heteroaryl, and optionally substituted $C_{3-6}$ heterocyclyl;
$R_9$ is selected from the group consisting of hydrogen and optionally substituted $C_{1-6}$ alkyl;
$R_{10}$ is selected from the group consisting of hydrogen, $C_{1-6}$ alkyl and $C_{3-8}$ cycloalkyl; or
$R_9$ and $R_{10}$ are taken together with the nitrogen to which they are attached form a 4 to 7 membered, saturated, ring optionally having 1 additional ring heteroatom selected from the group N, O, and S and optionally substituted on any of the ring carbon atoms with 1 to 5 substituents independently selected from the group consisting of cyano, halo, hydroxy, amino, optionally substituted $C_{3-6}$ heterocyclyl, $C_{1-9}$ amide, optionally substituted $C_{1-6}$ alkyl, and $C_{1-4}$ alkoxy and substituted on any additional ring nitrogen by a substituent selected from the group consisting of hydrogen, $C_{3-8}$ cycloalkyl, and optionally substituted $C_{1-6}$ alkyl;
$R_{11}$ is selected from the group consisting of hydrogen, $C_{1-6}$ alkyl, and $C_{3-8}$ cycloalkyl; or a pharmaceutically acceptable salt thereof.

The present invention also provides pharmaceutical compositions, comprising: a compound of formula I or a pharmaceutically acceptable salt thereof and a pharmaceutically acceptable excipient.

The compounds of the present invention are modulators of GPR6 and are useful to treat a variety of neurological and psychiatric disorders, for example movement disorders including Parkinson's disease, levodopa induced dyskinesias, and Huntington's disease, drug addiction, eating disorders, cognitive disorders, schizophrenia, bipolar disorders, and depression. Thus, the present invention also provides methods of treating the conditions associated with GPR6 described herein comprising, administering to a patient in need thereof an effective amount of the compounds of the invention. The present invention provides for the use of the compounds of the invention as a medicament, including for treatment of the conditions associated with GPR6 described herein, and including for the manufacture of a medicament for treating the conditions associated with GPR6 described herein.

The present invention also provides processes from making GPR6 modulators and intermediates thereof.

DETAILED DESCRIPTION OF THE INVENTION

The term "$C_{1-4}$ alkyl" refers to a straight or branched alkyl chain of one to four carbon atoms.

The term "optionally substituted $C_{1-4}$ alkyl" refers to a $C_{1-4}$ alkyl optionally substituted with 1 to 6 substituents independently selected from the group consisting of optionally substituted $C_{1-4}$ alkoxy, $C_{1-4}$ thioalkoxy, $C_{1-9}$ amide, $C_{1-7}$ amido, amino, $C_{1-8}$ alkylamino, $C_{1-5}$ oxycarbonyl, $C_{1-5}$ carbonyloxy, $C_{1-8}$ sulfonyl, cyano, optionally substituted $C_{3-8}$ cycloalkyl, $C_{3-8}$ cycloalkoxy, halo, hydroxy, nitro, oxo, optionally substituted $C_{3-6}$ heterocyclyl, optionally substituted $C_{1-10}$ heteroaryl, and optionally substituted $C_{6-10}$ aryl.

More particularly "optionally substituted $C_{1-4}$ alkyl" refers to a $C_{1-4}$ alkyl optionally substituted with 1 to 6 substituents independently selected from the group consisting of $C_{1-4}$ alkoxy, $C_{1-9}$ amide, amino, $C_{1-8}$ alkylamino, $C_{1-5}$ oxycarbonyl, cyano, $C_{3-8}$ cycloalkyl, halo, hydroxy, $C_{3-6}$ heterocyclyl optionally substituted on any ring nitrogen by $C_{1-4}$ alkyl, $C_{1-10}$ heteroaryl, and optionally substituted phenyl.

Even more particularly "optionally substituted $C_{1-4}$ alkyl" refers to a $C_{1-4}$ alkyl optionally substituted with 1 to 6 substituents independently selected from the group consisting of $C_{1-4}$ alkoxy, cyano, $C_{3-8}$ cycloalkyl, halo, hydroxy, $C_{3-6}$ heterocyclyl optionally substituted on any ring nitrogen by $C_{1-4}$ alkyl, and optionally substituted phenyl.

The term "$C_{1-6}$ alkyl" refers to a straight or branched alkyl chain of one to six carbon atoms.

The term "optionally substituted $C_{1-6}$ alkyl" refers to a $C_{1-6}$ alkyl optionally substituted with 1 to 7 substituents independently selected from the group consisting of amino, $C_{1-8}$ alkylamino, optionally substituted $C_{1-4}$ alkoxy, $C_{1-4}$ thioalkoxy, $C_{1-9}$ amide, $C_{1-7}$ amido, $C_{1-5}$ oxycarbonyl, $C_{1-5}$ carbonyloxy, $C_{1-8}$ sulfonyl, cyano, optionally substituted $C_{3-8}$ cycloalkyl, halo, hydroxy, oxo, optionally substituted $C_{1-10}$ heteroaryl, optionally substituted $C_{3-6}$ heterocyclyl, and optionally substituted $C_{6-10}$ aryl.

More particularly "optionally substituted $C_{1-6}$ alkyl" refers to a $C_{1-6}$ alkyl optionally substituted with 1 to 7 substituents independently selected from the group consisting of $C_{1-4}$ alkoxy, $C_{1-9}$ amide, amino, $C_{1-8}$ alkylamino, $C_{1-5}$ oxycarbonyl, cyano, $C_{3-8}$ cycloalkyl, halo, hydroxy, $C_{3-6}$ heterocyclyl optionally substituted on any ring nitrogen by $C_{1-4}$ alkyl, $C_{1-10}$ heteroaryl, and optionally substituted phenyl.

Even more particularly "optionally substituted $C_{1-6}$ alkyl" refers to a $C_{1-6}$ alkyl optionally substituted with 1 to 7 substituents independently selected from the group consisting of $C_{1-4}$ alkoxy, cyano, $C_{3-8}$ cycloalkyl, halo, hydroxy, $C_{3-6}$ heterocyclyl optionally substituted on any ring nitrogen by $C_{1-4}$ alkyl, and optionally substituted phenyl.

The term "$C_{1-6}$ haloalkyl" refers to a straight or branched alkyl chain of one to six carbon atoms substituted with 1 to 3 halogen atoms. More particularly, the term "$C_{1-6}$ haloalkyl" refers fluoromethyl and difluoromethyl.

The term "$C_{1-8}$ sulfonyl" refers to a sulfonyl linked to a $C_{1-6}$ alkyl group, $C_{3-8}$ cycloalkyl, or an optionally substituted phenyl.

The term "$C_{1-6}$ alkylene" refers to a straight or branched, divalent, alkylene chain of one to six carbon atoms.

The term "$C_{1-6}$ haloalkylene" refers to a straight or branched, divalent, alkylene chain of one to six carbon atoms substituted with 1 to 3 halogen atoms. More particularly, the term "$C_{1-6}$ haloalkylene" refers fluoromethylene and difluoromethylene.

The term "$C_{1-4}$ alkoxy" refers to a $C_{1-4}$ alkyl attached through an oxygen atom.

The term "optionally substituted $C_{1-4}$ alkoxy" refers to a $C_{1-4}$ alkoxy optionally substituted with 1 to 6 substituents independently selected from the group consisting of $C_{1-4}$ alkoxy, $C_{1-9}$ amide, $C_{1-5}$ oxycarbonyl, cyano, optionally substituted $C_{3-8}$ cycloalkyl, halo, hydroxy, optionally substituted $C_{1-10}$ heteroaryl, and optionally substituted $C_{6-10}$ aryl. While it is understood that where the optional substituent is $C_{1-4}$ alkoxy or hydroxy then the substituent is generally not alpha to the alkoxy attachment point, the term "optionally substituted $C_{1-4}$ alkoxy" includes stable moieties and specifically includes trifluoromethoxy, difluoromethoxy, and fluoromethoxy.

More particularly "optionally substituted $C_{1-4}$ alkoxy" refers to a $C_{1-4}$ alkoxy optionally substituted with 1 to 6 substituents independently selected from the group consisting of $C_{1-4}$ alkoxy, cyano, $C_{3-8}$ cycloalkyl, halo, hydroxy, and optionally substituted phenyl. Even more particularly "optionally substituted $C_{1-4}$ alkoxy" refers to trifluoromethoxy, difluoromethoxy, and fluoromethoxy.

The term "$C_{1-9}$ amide" refers to a —C(O)NR$_a$R$_b$ group in which R$_a$ is selected from the group consisting of hydrogen and $C_{1-4}$ alkyl, and R$_b$ is selected from the group consisting of hydrogen, $C_{1-3}$ alkyl, and optionally substituted phenyl.

The term "$C_{1-7}$ amido" refers to a —NHC(O)R$_c$ group in which R$_c$ is selected from the group consisting of hydrogen, $C_{1-6}$ alkyl, and optionally substituted phenyl.

The term "$C_{1-5}$ carbamoyl" refers to an O- or N-linked carbamate substituted with a terminal $C_{1-4}$ alkyl.

The term "$C_{1-5}$ ureido" refers to a urea optionally substituted with a $C_{1-4}$ alkyl.

The term "$C_{1-8}$ alkylamino" refers to a —NR$_d$R$_e$ group in which R$_d$ is a $C_{1-4}$ alkyl and R$_e$ is selected from the group consisting of hydrogen and $C_{1-4}$ alkyl.

The term "$C_{6-10}$ aryl" refers to a monocyclic and polycyclic unsaturated, conjugated hydrocarbon having five to ten carbon atoms, and includes phenyl, and naphthyl.

More particularly "$C_{6-10}$ aryl" refers to phenyl.

The term "optionally substituted $C_{6-10}$ aryl" refers to a $C_{6-10}$ aryl optionally substituted with 1 to 5 substituents independently selected from the group consisting of optionally substituted $C_{1-4}$ alkyl, optionally substituted $C_{1-4}$ alkoxy, $C_{1-4}$ thioalkoxy, amino, $C_{1-8}$ alkylamino, $C_{1-9}$ amide, $C_{1-7}$ amido, $C_{1-5}$ oxycarbonyl, $C_{1-5}$ carbonyloxy, $C_{1-8}$ sulfonyl, $C_{1-5}$ carbamoyl, $C_{1-6}$ sulfonylamido, aminosulfonyl, $C_{1-10}$ aminosulfonyl, $C_{1-5}$ ureido, cyano, halo, and hydroxyl.

More particularly "optionally substituted $C_{640}$ aryl" refers to a $C_{6-10}$ aryl optionally substituted with 1 to 5 substituents independently selected from the group consisting of $C_{1-4}$ alkyl, $C_{1-4}$ alkoxy, cyano, halo, hydroxy, amino, trifluoromethyl, and trifluoromethoxy.

Even more particularly "optionally substituted $C_{6-10}$ aryl" refers to phenyl optionally substituted with 1 to 5 substituents independently selected from the group consisting of $C_{1-4}$ alkyl, $C_{1-4}$ alkoxy, cyano, halo, trifluoromethyl, and trifluoromethoxy.

The term "$C_{1-5}$ oxycarbonyl" refers to an oxycarbonyl group (—$CO_2H$) and $C_{1-4}$ alkyl ester thereof.

The term "$C_{1-5}$ carbonyloxy" refers to a carbonyloxy group (—$O_2CR_f$), in which $R_f$ is selected from the group consisting of hydrogen and $C_{1-4}$ alkyl, for example, acetoxy.

The term "$C_{3-8}$ cycloalkyl" refers to monocyclic or bicyclic, saturated or partially (but not fully) unsaturated alkyl ring of three to eight carbon atoms, and includes cyclopropyl, cyclobutyl, cyclopentyl, cyclohexyl, and the like. It is understood that the term includes benzofused cyclopentyl and cyclohexyl.

The term "optionally substituted $C_{3-8}$ cycloalkyl" refers to a $C_{3-8}$ cycloalkyl optionally substituted with 1 to 6 substituents independently selected from the group consisting of optionally substituted $C_{1-4}$ alkyl, optionally substituted $C_{1-4}$ alkoxy, $C_{1-9}$ amide, $C_{1-7}$ amido, amino, $C_{1-8}$ alkylamino, $C_{1-5}$ oxycarbonyl, cyano, $C_{3-8}$ cycloalkyl, $C_{3-8}$ cycloalkoxy, halo, hydroxy, nitro, oxo, optionally substituted $C_{1-10}$ heteroaryl, and optionally substituted phenyl.

More particularly "optionally substituted $C_{3-8}$ cycloalkyl" refers to a $C_{3-8}$ cycloalkyl optionally substituted with 1 to 3 substituents independently selected from the group consisting of $C_{1-4}$ alkoxy, halo, hydroxy, and $C_{1-4}$ alkyl optionally substituted with $C_{1-4}$ alkoxy, halo, and hydroxy.

The term "$C_{3-8}$ cycloalkoxy" refers to a $C_{3-8}$ cycloalkyl attached through and oxygen.

The terms "halogen" and "halo" refers to a chloro, fluoro, bromo or iodo atom.

The term "$C_{3-6}$ heterocyclyl" refers to a 4 to 8 membered monocyclic or bicyclic, saturated or partially (but not fully) unsaturated ring having one or two heteroatoms selected from the group consisting of nitrogen, oxygen, and sulfur and the ring optionally includes a carbonyl to form a lactam or lactone. It is understood that where sulfur is included that the sulfur may be either —S—, —SO—, and —$SO_2$—. It is also under that the term includes spirofused bicyclic systems. For example, but not limiting, the term includes azetidinyl, pyrrolidinyl, piperidinyl, piperazinyl, morpholinyl, thiomorpholinyl, oxetanyl, dioxolanyl, tetrahydropyranyl, tetrahydrothiopyranyl, tetrahydrofuryl, hexahydropyrimidinyl, tetrahydropyrimidinyl, dihydroimidazolyl, and the like. It is understood that a $C_{3-6}$ heterocyclyl can be attached as a substituent through a ring carbon or a ring nitrogen atom.

More particularly "$C_{3-6}$ heterocyclyl" is selected from the group consisting of azetidinyl, pyrrolidinyl, piperidinyl, piperazinyl, morpholinyl, oxetanyl, tetrahydropyranyl, tetrahydrothiopyranyl, and tetrahydrofuryl.

The term "optionally substituted $C_{3-6}$ heterocyclyl" refers to a $C_{3-6}$ heterocyclyl optionally substituted on the ring carbons with 1 to 4 substituents independently selected from the group consisting of optionally substituted $C_{1-4}$ alkyl, optionally substituted $C_{1-4}$ alkoxy, $C_{1-9}$ amide, $C_{1-7}$ amido, amino, $C_{1-8}$ alkylamino, $C_{1-5}$ oxycarbonyl, cyano, optionally substituted $C_{3-8}$ cycloalkyl, $C_{3-8}$ cycloalkoxy, halo, hydroxy, nitro, oxo, and optionally substituted phenyl; and optionally substituted on any ring nitrogen with a substituent independently selected from the group consisting of optionally substituted $C_{1-4}$ alkyl, $C_{3-8}$ cycloalkyl, optionally substituted $C_{3-6}$ heterocyclyl, optionally substituted $C_{1-10}$ heteroaryl, and optionally substituted phenyl.

More particularly "optionally substituted $C_{3-6}$ heterocyclyl" refers to a $C_{3-6}$ heterocyclyl optionally substituted on the ring carbons with 1 to 4 substituents independently selected from the group consisting of $C_{1-4}$ alkyl, $C_{1-4}$ alkoxy, halo, and hydroxy and optionally substituted on any ring nitrogen with a $C_{1-4}$ alkyl.

The term "$C_{1-10}$ heteroaryl" refers to a five to thirteen membered, monocyclic or polycyclic fully unsaturated, ring or ring system with one to ten carbon atoms and one or more, typically one to four, heteroatoms selected from the group consisting of nitrogen, oxygen, and sulfur. For example, but not limiting, the term includes furyl, thienyl, pyrrolyl, imidazolyl, isothiazolyl, isoxazolyl, oxadiazolyl, oxazolyl, thiazolyl, thiadiazolyl, triazolyl, tetrazolyl, pyrazinyl, pyrazolyl, pyridazinyl, pyridyl, pyrimidyl, azepinyl, diazepinyl, benzazepinyl, benzodiazepinyl, benzofuryl, benzothienyl, indolyl, isoindolyl, benzimidazolyl, benzisothiazolyl, benzisoxazolyl, benzoxadiazolyl, benzoxazolyl, benzopyrazinyl, benzopyrazolyl, imidazopyridyl, pyrazolopyridyl, pyrrolopyridyl, quinazolyl, thienopyridyl, imidazopyridyl, quinolyl, isoquinolyl benzothiazolyl, and the like. It is understood that a $C_{1-10}$ heteroaryl can be attached as a substituent through a ring carbon or a ring nitrogen atom where such an attachment mode is available, for example for a pyrrolyl, indolyl, imidazolyl, pyrazolyl, azepinyl, triazolyl, pyrazinyl, etc.

More particularly "$C_{1-10}$ heteroaryl" is selected from the group consisting of furyl, thienyl, pyrrolyl, imidazolyl, oxazolyl, thiazolyl, pyrazolyl, triazolyl, pyridyl, and pyrimidyl.

The term "optionally substituted $C_{1-10}$ heteroaryl" refers to a $C_{1-10}$ heteroaryl optionally substituted with 1 to 5 substituents on carbon independently selected from the group consisting of amino, $C_{1-8}$ alkylamino, $C_{1-9}$ amide, $C_{1-7}$ amido, $C_{1-5}$ carbamoyl, $C_{1-6}$ sulfonylamido, aminosulfonyl, $C_{1-10}$ aminosulfonyl, $C_{1-5}$ ureido, optionally substituted $C_{1-4}$ alkyl, optionally substituted $C_{1-4}$ alkoxy, cyano, halo, hydroxyl, oxo, nitro, $C_{1-5}$ carbonyloxy, $C_{1-5}$ oxycarbonyl, and $C_{1-8}$ sulfonyl and optionally substituted with a substituent on each nitrogen independently selected from the group consisting of optionally substituted $C_{1-4}$ alkyl, $C_{1-8}$ sulfonyl, optionally substituted $C_{3-6}$ heterocyclyl, and optionally substituted phenyl.

More particularly "optionally substituted $C_{1-10}$ heteroaryl" refers to a $C_{1-10}$ heteroaryl optionally substituted with 1 to 3 substituents on carbon independently selected from the group consisting of amino, $C_{1-8}$ alkylamino, $C_{1-9}$ amide, $C_{1-4}$ alkyl, $C_{1-4}$ alkoxy, cyano, halo, hydroxyl, oxo, trifluoromethyl, and trifluoromethoxy and optionally substituted on a ring nitrogen with a $C_{1-4}$ alkyl.

Even more particularly "optionally substituted $C_{1-10}$ heteroaryl" refers to a $C_{1-10}$ heteroaryl selected from the group consisting of furyl, thienyl, pyrrolyl, imidazolyl, oxazolyl, thiazolyl, pyrazolyl, diazolyl, pyridyl, pyrimidyl, and triazolyl each optionally substituted with 1 to 3 substituents independently selected from the group consisting of $C_{1-4}$ alkyl, $C_{1-4}$ alkoxy, cyano, halo, trifluoromethyl, and trifluoromethoxy and optionally substituted on a ring nitrogen with a methyl.

The term "oxo" refers to an oxygen atom doubly bonded to the carbon to which it is attached to form the carbonyl of a ketone or aldehyde. For example, a pyridone radical is contemplated as an oxo substituted $C_{1-10}$ heteroaryl.

The term "optionally substituted phenyl" refers to a phenyl group optionally substituted with 1 to 5 substituents independently selected from the group consisting of $C_{1-4}$ alkyl, $C_{1-4}$ alkoxy, $C_{1-9}$ amide, amino, $C_{1-8}$ alkylamino, $C_{1-5}$ oxycarbonyl, cyano, halo, hydroxyl, nitro, $C_{1-8}$ sulfonyl, and trifluoromethyl.

More particularly "optionally substituted phenyl" refers to a phenyl group optionally substituted with 1 to 5 substituents independently selected from the group consisting of $C_{1-4}$ alkyl, $C_{1-4}$ alkoxy, $C_{1-9}$ amino, $C_{1-8}$ alkylamino, $C_{1-5}$ oxycarbonyl, cyano, halo, hydroxyl, nitro, and trifluoromethyl.

The term "$C_{1-6}$ sulfonylamido" refers to a $—NHS(O)_2—R_g$ group wherein $R_g$ is selected from the group consisting of $C_{1-6}$ alkyl and optionally substituted phenyl.

The term "aminosulfonyl" refers to a $—S(O)_2NH_2$.

The term "$C_{1-10}$ aminosulfonyl" refers to a $—S(O)_2NR_hR_i$ group wherein $R_h$ is selected from the group consisting of hydrogen and $C_{1-4}$ alkyl and $R_i$ is selected from the group consisting of $C_{1-4}$ alkyl, and optionally substituted phenyl.

The term "$C_{1-4}$ thioalkoxy" refers to a $C_{1-4}$ alkyl attached through a sulfur atom.

The term "pharmaceutically acceptable salt" refers to salts of pharmaceutically acceptable organic acids and bases or inorganic acids and bases. Such salts are well known in the art and include those described in Journal of Pharmaceutical Science, 66, 2-19 (1977). An example is the hydrochloride salt.

The term "substituted," including when used in "optionally substituted" refers to one or more hydrogen radicals of a group are replaced with non-hydrogen radicals (substituent(s)). It is understood that the substituents may be either the same or different at every substituted position. Combinations of groups and substituents envisioned by this invention are those that are stable or chemically feasible.

The term "stable" refers to compounds that are not substantially altered when subjected to conditions to allow for their production. In a non-limiting example, a stable compound or chemically feasible compound is one that is not substantially altered when kept at a temperature of 40° C. or less, in the absence of moisture or other chemically reactive conditions, for about a week.

It is understood that, where the terms defined herein mention a number of carbon atoms, the mentioned number refers to the mentioned group and does not include any carbons that may be present in any optional substituent(s) thereon.

The skilled artisan will appreciate that certain of the compounds of the present invention exist as isomers. All stereoisomers of the compounds of the invention, including geometric isomers, enantiomers, and diastereomers, in any ratio, are contemplated to be within the scope of the present invention.

The skilled artisan will appreciate that certain of the compounds of the present invention exist as tautomers. All tautomeric forms the compounds of the invention are contemplated to be within the scope of the present invention.

Compounds of the invention also include all pharmaceutically acceptable isotopic variations, in which at least one atom is replaced by an atom having the same atomic number, but an atomic mass different from the predominant atomic mass. Isotopes suitable for inclusion in compounds of formula I include radioactive isotopes.

The terms "compounds of the invention" and "a compound of the invention" and "compounds of the present invention", and the like include the embodiment of formula I and the other more particular embodiments encompassed by formula I described herein and exemplified compounds described herein and a pharmaceutically acceptable salt of each of these embodiments.

(a) One embodiment relates to compounds of formula I wherein $X_1$ is CH and $X_2$ is N.

(b) One embodiment relates to compounds of formula I wherein $X_1$ is N and $X_2$ is N.

(c) One embodiment relates to compounds of formula I and embodiment (a) and (b) wherein an $R_4$ is cyano.

(d) One embodiment relates to compounds of formula I and embodiment (a) and (b) $R_4$ is selected from the group cyano, $—C(O)—N(R_9)(R_{10})$, and $—C(O)—OR_{11}$.

(e) One embodiment relates to compounds of formula I and embodiments (a), (b), (c), and (d) wherein $R_1$ is optionally substituted $C_{6-10}$ aryl.

(f) One embodiment relates to compounds of formula I and embodiments (a), (b), (c), and (d) wherein Z is $C_{1-6}$ alkylene.

(g) One embodiment relates to compounds formula I and embodiments (a), (b), (c), and (d) wherein Z is $C_{1-6}$ haloalkylene.

(h) One embodiment relates to compounds formula I and embodiments (a), (c), and (d) wherein Z is —O—.

(i) One embodiment relates to compounds of formula I and embodiments (a), (b), (c), and (d) wherein Z is —C(O)—.

(j) One embodiment relates to compounds of formula I and embodiments (a), (b), (c), (d), (e), (f), (g), (h), and (i) wherein $R_2$ is $—NR_6R_7$. In another embodiment within embodiment (j), $R_6$ is hydrogen and $R_7$ is $C_{1-6}$ alkyl. In yet another embodiment within embodiment (j), $R_6$ is hydrogen and $R_7$ is $C_{3-8}$ cycloalkyl. In yet another embodiment within embodiment (j), $R_6$ is hydrogen and $R_7$ is $C_{3-6}$ heterocyclyl.

(k) One embodiment relates to compounds of formula I and embodiments (a), (b), (c), (d), (e), (f), (g), (h), (i), and (j) wherein s is 1.

(l) One embodiment relates to compounds of formula I and embodiments (a), (b), (c), (d), (e), (f), (g), (h), (i), (j), and (k) wherein q is 1.

(m) One embodiment relates to compounds of formula I and embodiments (a), (b), (c), (d), (e), (f), (g), (h), (i), (j), (k), and (1) wherein $R_4$ is cyano and r is 2.

(m) One embodiment relates to compounds of formula I and embodiments (a), (b), (c), (d), (e), (f), (g), (h), (i), (j), (k), and (1) wherein r is 1.

(ay) Another embodiment relates to a pharmaceutically acceptable salt of each of the above embodiments.

(az) Another embodiment relates to a pharmaceutically acceptable salt of each of the exemplified compounds.

The compounds of the invention can be prepared by a variety of procedures, some of which are described below. All substituents, unless otherwise indicated, are as previously defined. The products of each step can be recovered by conventional methods including extraction, evaporation, precipitation, chromatography, filtration, trituration, crystallization, and the like. The procedures may require protection of certain groups, for example hydroxy, amino, or carboxy groups to minimize unwanted reactions. The selection, use, and removal of protecting groups are well known and appreciated as standard practice, for example T. W. Greene and P. G. M. Wuts in Protective Groups in Organic Chemistry (John Wiley and Sons, 1991). In the schemes below starting materials are either commercially available or can be ready prepared by methods well known in the art.

Scheme A

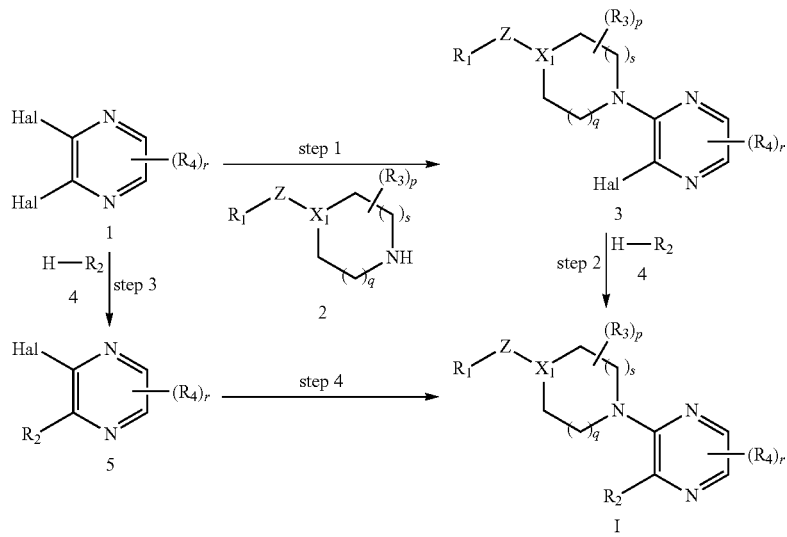

Scheme A depicts the formation of compounds in which $X_2$ is N.

In Scheme A, step 1, an appropriate compound of formula 1 is contacted with an appropriate compound of formula 2 to give a compound of formula 3. An appropriate compound of formula 1 is one in which Hal is a halogen and $R_4$ and r are as desired in the final compound of formula I. An appropriate compound of formula 2 is one in which $R_1$, Z, $R_3$, p, s, and q are as desired in the final compound of formula I or give rise to $R_1$, Z, and $R_3$ as desired in the final compound of formula I. Compounds of formula 2 are either commercially available or they can be readily prepared by methods well known in the art. For example, compounds of formula 2 where Z is oxygen can be prepared by Mitsunobu reaction between a piperidinol and an aryl alcohol.

The reaction is carried out in a suitable organic solvent like dioxane, n-butanol, dimethyl sulfoxide and the like with or without base such as diisopropylethylamine and triethylamine. The reaction is generally carried out at a temperature of from 0 to 80° C.

It is understood that a compound of formula 1 can also be treated with piperazine to give rise to compounds in which $X_1$ is N. The piperazine derivative can be further modified by reductive amination, alkylation, arylation, amidation, sulfonylation and the like to provide a compound of formula 3. Also the piperazine can be protected and elaborated as mentioned above after deprotection in a later step if desired.

In Scheme A, step 2, a compound of formula 3 is contacted with an appropriate compound of formula 4 to give a compound of formula I. An appropriate compound of formula 4 is $HOR_5$ or $HNR_6R_7$ in which $R_5$ or $R_6$ and $R_7$ are as desired in the final compound of formula I.

Where the compound of formula 4 is an amine, $HNR_6R_7$, the reaction is carried out in a suitable organic solvent like dioxane, ethanol, tetrahydrofuran, dimethyl sulfoxide, N,N-dimethylformamide and the like, with or without a base such as sodium hydroxide, diisopropylethylamine or triethylamine. The reaction is generally carried out at temperature between 20 to 150° C.

Where the compound of formula 4 is an alcohol, $HOR_5$, the reaction is carried out in a suitable organic solvent like dioxane, tetrahydrofuran, dimethyl sulfoxide, N,N-dimethylformamide and the like, with a base such as sodium hydride, lithium hydride, potassium t-butoxide, and the like. The reaction is generally carried out at temperature between 0 to 150° C.

Alternatively, as depicted in Scheme A, step 3, using the methodology described above, an appropriate compound of formula 1 can be contacted with an appropriate compound of formula 2 to give a compound of formula 5.

As depicted in Scheme A, step 4, a compound of formula 5 can be contacted with a compound of formula 2 to give a compound of formula I.

It will be recognized by one of ordinary skill in the art that the steps in Scheme A may be varied to provide compounds of formula I. In particular, the order of the steps required to produce the compounds of formula I is dependent upon the particular compound being synthesized, the starting compound, and the relative lability of the substituted moieties. Other variations are possible and are readily understood by the skilled person.

Scheme B

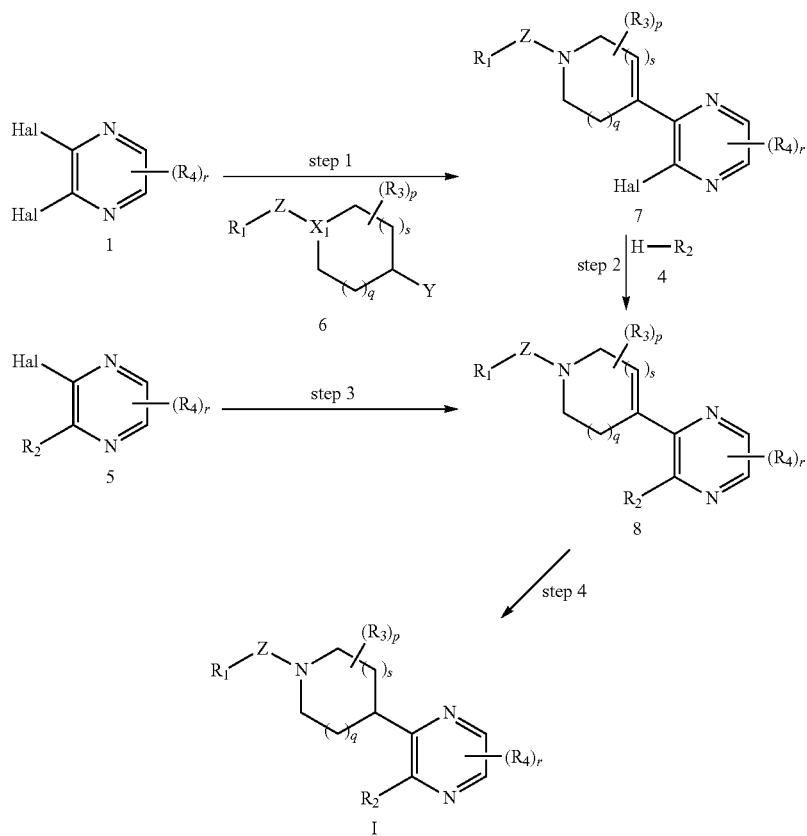

Scheme B depicts the formation of compounds in which $X_2$ is CH.

In Scheme B, step 1, an appropriate compound of formula 1, as described above, is contacted with an appropriate compound of formula 6 to give a compound of formula 7. An appropriate compound of formula 6 is one in which $R_1$, Z, $R_3$, p, s, and q are as desired in the final compound of formula I or give rise to $R_1$, Z, and $R_3$ as desired in the final compound of formula I and Y a boronic acid or boronic ester. It is also understood that the group depicted as $R_1$—Z— can be replaced by an appropriate protecting group, such a methyl, benzyl, t-BOC, or Cbz, subsequent removal of the protecting group and installation of $R_1$—Z— as desired in the final product of formula I.

Such reactions are generally known as a Suzuki reaction and are well known in the art. While a Suzuki reaction is depicted in Scheme B it is understood that other carbon-carbon bond forming coupling reactions can be used with compounds of formula 6 having Y other than boronic acid or esters to produce compounds of formula I.

In Scheme B, step 2, a compound of formula 7 is contacted with an appropriate compound of formula 4 to give a compound of formula 8. An appropriate compound of formula 4 and general reaction conditions are described above in Scheme A, step 2.

Alternately, Scheme B, step 3, depicts Suzuki reaction with an appropriate compound of formula 6 and an appropriate compound of formula 5 as described above to give a compound of formula 8.

In Scheme B, step 4, a compound of formula 8 is reduced to a compound of formula I. Such reductions are well known in the art. The reaction is carried out in a suitable organic solvent like dioxane, ethanol, methanol, isopropanol, tetrahydrofuran, and the like. The reaction is generally carried out using hydrogen and a catalyst, such as platinum or palladium catalyst.

It will be recognized by one of ordinary skill in the art that the steps in Scheme B may be varied to provide compounds of formula I. In particular, the order of the steps required to produce the compounds of formula I is dependent upon the particular compound being synthesized, the starting compound, and the relative lability of the substituted moieties.

It is also understood that some compounds of formula I may be elaborated to other compounds of formula I, in an additional steps not shown. Compounds of formula I may be elaborated in a variety of ways. Such reactions include hydrolysis, oxidation, reduction, alkylation, amidations, and the like. Also, in an optional step, not shown in the schemes above, the compounds of formula I can be converted to pharmaceutically acceptable salts by methods well known and appreciated in the art.

The following examples are intended to be illustrative and non-limiting, and represent specific embodiments of the present invention.

Proton nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). Other abbreviations have their usual meaning unless otherwise indicated. The mass spectra, unless otherwise indicated, were recorded using either electrospray ionization (ESI) or atmospheric pressure chemical ionization.

The examples below were carried out in appropriate vessels and were typically stirred. Where indicated, products of certain preparations and examples are purified by HPLC. Where indicated products of the preparations and examples were purified by HPLC.

HPLC Method A: Pump: Shimadzu LC-8A; UV/Vis: SPD-20A; Software: LCSolution. A Phenomenex Gemini® C18, 5 µm, ID 30×100 mm column was used and eluted with gradients of ACN (containing 0.035% TFA) and water (containing 0.005% TFA). A 10% to 100% ACN gradient was used unless otherwise indicated.

HPLC Method B: Pump: Waters 2525 or 2545; MS: ZQ; Software: MassLynx. A Xbridge™ C18, 5 µm, ID 30×75 mm column was used and eluted with gradients of ACN (containing 0.035% TFA) and water (containing 0.005% TFA).

After isolation by chromatography, the solvent is removed and the product is obtained by evaporating product containing fractions (e.g., GeneVac™), rotary evaporator, evacuated flask, lyophilization, etc.

The abbreviations used throughout have their conventional meanings unless indicated otherwise. For example, the following abbreviations will be used: ACN (acetonitrile); aq (aqueous); Boc or t-BOC (tert-butoxycarbonyl); Cbz (carbobenzyloxy); DCM (dichloromethane); DMSO (dimethyl sulfoxide); TFA (trifluoroacetic acid); HOAc (acetic acid), MeOH (methanol), PE (petroleum ether), EA or EtOAc (ethyl acetate) and the like.

Preparation 1
(5-chloro-2-fluorophenyl)(piperidin-4-yl)methanone

A solution of 2-bromo-4-chloro-1-fluorobenzene (175 µL, 1.377 mmol) in THF (4.59 mL) at 78° C. was treated with n-BuLi (2.6 M, 741 µL, 1.928 mmol) and the reaction mixture was stirred for 30 min. To this was added tert-butyl 4-(methoxy(methyl)carbamoyl)piperidine-1-carboxylate (250 mg, 0.918 mmol) in one portion. The cooling bath was removed and the resulting reaction mixture was allowed to warm to rt and stirred for 1.5 h. Purification by automated flash silica gel chromatography using 10% EtOAc in hexanes afforded tert-butyl 4-(5-chloro-2-fluorobenzoyl)piperidine-1-carboxylate (287.9 mg, 92%) as a yellow oil. ESI-MS m/z [M+Na]+ 364.20.

A solution of tert-butyl 4-(5-chloro-2-fluorobenzoyl)piperidine-1-carboxylate (287.9 mg, 0.843 mmol) in dioxane (2.41 mL) was treated with HCl (2.11 mL, 8.43 mmol) at rt and the resulting reaction mixture was stirred overnight. The reaction mixture was diluted with hexanes and filtered by suction to afford (5-chloro-2-fluorophenyl)(piperidin-4-yl)methanone as its HCl salt (146 mg, 62.3%) as a yellow solid. ESI-MS m/z [M+H]+ 242.20.

Preparation 2 4-(2,4-difluorophenoxy)piperidine

To a solution of 2,4-difluorophenol (10 g, 77 mmol), PPh3 (30.2 g, 115 mmol) and tert-butyl 4-hydroxypiperidine-1-carboxylate (30.9 g, 154 mmol) in THF (400 mL) was added DEAD (18.3 mL, 115 mmol) at 0° C. dropwise. After the addition was completed, the resulting mixture was allowed to stir at 40° C. for 16 h. The mixture was poured into water and extracted with EtOAc (3×400 mL). The combined organic layers were dried over Na2SO4, filtered and concentrated to give the crude product. Purification by flash silica gel chromatography, eluting with 80:1 PE: EtOAc, gave tert-butyl 4-(2,4-difluorophenoxy)piperidine-1-carboxylate as an oil (20 g, 83%).

A solution of tert-butyl 4-(2,4-difluorophenoxy)piperidine-1-carboxylate (20 g, 63.8 mmol) in 4:1 HCl/EtOAc (250 mL) was stirred at 25° C. for 1 h. The mixture was concentrated to give the title compound, as its HCl salt, as a white solid (15.4 g, 97%). 1H NMR (400 MHz, DMSO-d6) δ ppm 1.84 (m, 2H), 2.08 (m, 2H), 3.05 (m, 2H), 3.20 (m, 2H), 4.57 (m, 1H), 7.04 (m, 1H), 7.31 (m, 2H), 8.95 (br d, 2H).

Preparation 3
3-fluoro-4-(piperidin-4-yloxy)benzonitrile

A solution of 3,4-difluorobenzonitrile (28 g, 201 mmol) and tert-butyl 4-hydroxypiperidine-1-carboxylate (40.5 g, 201 mmol) in THF (500 mL) was treated with sodium hydride (4 g, 100 mmoL) and stirred at 25° C. for 16 h. The reaction mixture was washed with water, extracted with EtOAc, and the crude product purified by flash silica gel chromatography gave tert-butyl 4-(4-cyano-2-fluorophenoxy)piperidine-1-carboxylate (25 g, 39%).

A solution of tert-butyl 4-(4-cyano-2-fluorophenoxy)piperidine-1-carboxylate (42 g, 131 mmol) dissolved in 4:1 HCl/EtOAc (100 mL) was stirred for 5 h. The mixture was concentrated to give the title compound as its HCl salt (12 g, 36%). 1H NMR (400 MHz, DMSO-d6) δ ppm 1.89 (m, 2H), 2.14 (m, 2H); 3.08 (m, 2H), 3.21 (m, 2H), 4.86 (m, 1H), 7.48 (t, J=8.4 Hz, 1H), 7.70 (d, J=8.4 Hz, 1H), 7.89 (m, 1H); ESI-MS m/z [M+H]+ 220.7.

Preparation 4
4-((2,4-difluorophenyl)fluoromethyl)piperidine

To a 0° C. solution of tert-butyl 4-(2,4-difluorobenzoyl)piperidine-1-carboxylate (1.28 g, 3.93 mmol) in MeOH (15.7 mL) was added NaBH4 (0.372 g, 9.84 mmol). The ice bath was removed and the reaction mixture stirred for 2 h at room temperature then was quenched with saturated aqueous NH4Cl. The organic layer was extracted with EtOAc, washed with H2O 2O and dried over MgSO4. The solvent was removed under reduced pressure gave tert-butyl 4-((2,4-difluorophenyl)(hydroxy)methyl)piperidine-1-carboxylate as a white hygroscopic solid.

To a 78° C. solution of tert-butyl 4-((2,4-difluorophenyl)(hydroxy)methyl)piperidine-1-carboxylate (200 mg, 0.611 mmol) in DCM (3.055 mL) was added DAST (242 µL, 1.833 mmol). The mixture was stirred at 78° C. for 30 min, then quenched with MeOH. Flash silica gel chromatography using a gradient of 0% to 100% EtOAc in hexanes gave tert-butyl 4-((2,4-difluorophenyl)fluoromethyl)piperidine-1-carboxylate as a colorless oil.

To a solution of racemic tert-butyl 4-((2,4-difluorophenyl) fluoromethyl)piperidine-1-carboxylate (148 mg, 0.449 mmol) in dioxane (1.50 mL) was added HCl (4 M in dioxane, 337 µL, 1.348 mmol). The mixture was heated at 45° C. for 16 h then concentrated in vacuo to give the title compound as its HCl salt (109 mg, 91%) as a white solid.

Preparation 5
(R)-4-((2,4-difluorophenyl)fluoromethyl)piperidine tert-Butyl 4-((2,4-difluorophenyl)fluoromethyl)piperidine-1-carboxylate was subjected to chiral SFC separation to give (R)-tert-butyl 4-((2,4-difluorophenyl)fluoromethyl)piperidine-1-carboxylate.

(R)-tert-butyl 4-((2,4-difluorophenyl)fluoromethyl)piperidine-1-carboxylate (2.8 g, 8.50 mmol) was dissolved in EtOAc (20 mL) and HCl (4 M in EtOAc, 21 mL) was added. The reaction mixture was stirred at 23° C. for 2 h. Evaporation of the solvent gave the title compound as its HCl salt (2.1 g, 93%). ESI-MS m/z [M+H]+ 229.9.

Preparation 6
(S)-4-((2,4-difluorophenyl)fluoromethyl)piperidine tert-Butyl 4-((2,4-difluorophenyl)fluoromethyl)piperidine-1-carboxylate as was subjected to chiral SFC separation to give (R)-tert-butyl 4-((2,4-difluorophenyl)fluoromethyl)piperidine-1-carboxylate. The HCl salt of the title compound was prepared in similar fashion to Preparation 5, using (S)-tert-butyl 4-((2,4-difluorophenyl)fluoromethyl)piperidine-1-carboxylate. ESI-MS m/z [M+H]+ 229.9.

Preparation 7 4-((2-fluorophenyl)sulfonyl)piperidine

A mixture of 2-fluorobenzenethiol (0.764 mL, 7.15 mmol), tert-butyl 4-((methylsulfonyl)oxy)piperidine-1-carboxylate (1.816 g, 6.5 mmol), and K2CO3 (1.348 g, 9.75 mmol) in ACN (16.25 mL) was heated at 80° C. overnight. The reaction mixture was poured into water and extracted twice with EtOAc. The combined organics were dried over Na2SO4, filtered, and concentrated under reduced pressure gave tert-butyl 4-((2-fluorophenyl)thio)piperidine-1-carboxylate as a yellow oil (1.98 g, 98%), which was carried forward without purification.

A solution of tert-butyl 4-((2-fluorophenyl)thio)piperidine-1-carboxylate (1.98 g, 6.36 mmol) in THF (54.5 mL) and MeOH (18.2 mL) at 0° C. was treated with a cold solution of Oxone® (9.77 g, 15.9 mmol) in water (54.5 mL). The reaction mixture was stirred for 5 h, gradually warming to room temperature. The reaction mixture was poured into water and extracted twice with EtOAc. The combined organics were washed with water and then saturated aqueous NaCl, dried over Na2SO4, filtered, and concentrated under reduced pressure. The residue was purified by flash silica gel chromatography using a gradient of 10% to 50% EtOAc with 0.1% triethylamine in heptanes gave tert-butyl 4-((2-fluorophenyl)sulfonyl)piperidine-1-carboxylate as a pale yellow oil (1.31 g, 60%).

A solution of tert-butyl 4-((2-fluorophenyl)sulfonyl)piperidine-1-carboxylate (1.31 g, 3.82 mmol) in dioxane (12.7 mL) at room temperature was treated with 4M HCl in dioxane (9.55 ml, 38.2 mmol). The reaction mixture was allowed to stir at room temperature overnight. The reaction mixture was concentrated under reduced pressure. The resulting white solid was triturated with hexanes, filtered, collected, and lyophilized overnight to give the title compound, as its HCl salt, as a white solid (815.1 mg, 76%). ESI-MS m/z [M+H]+ 243.95.

Preparation 8
4-((2-fluoro-4-methoxyphenyl)sulfonyl)piperidine

A mixture of 2,4-difluorobenzenethiol (0.810 mL, 7.15 mmol), tert-butyl 4-((methylsulfonyl)oxy)piperidine-1-carboxylate (1.816 g, 6.5 mmol), and K2CO3 (1.348 g, 9.75 mmol) in ACN (16.25 mL) was heated at 80° C. overnight. The reaction mixture was poured into water and extracted twice with EtOAc. The organic layer was dried over Na2SO4, filtered, and concentrated under reduced pressure to afford tert-butyl 4-((2,4-difluorophenyl)thio)piperidine-1-carboxylate (2.141 g) as a yellow oil, which was carried forward without purification.

A solution of tert-butyl 4-((2,4-difluorophenyl)thio)piperidine-1-carboxylate (2.141 g, 6.50 mmol) in THF/MeOH (3:1, 74 mL) at 0° C. was treated with a cold solution of Oxone® (9.99 g, 16.25 mmol) in water (56 mL). The reaction mixture was allowed to stir overnight, gradually warming to room temperature. The reaction mixture was poured into water and extracted twice with EtOAc. The combined organics were washed with water and then saturated aqueous NaCl, dried over Na2SO4, filtered, and concentrated under reduced pressure. The residue was purified by flash silica gel chromatography using a gradient of 10% to 40% EtOAc with 0.1% triethylamine in heptanes gave tert-butyl 4-((2,4-difluorophenyl)sulfonyl)piperidine-1-carboxylate (1.32 g, 56%) as a white solid. ESI-MS m/z [M+Na]+ 383.80.

To a suspension of tert-butyl 4-((2,4-difluorophenyl)sulfonyl)piperidine-1-carboxylate (50 mg, 0.138 mmol) in MeOH (461 µL) was added sodium methoxide (25.6 µL, 0.138 mmol, 5.4 M in MeOH) dropwise. The reaction mixture was allowed to stir at 45° C. for 20 min then concentrated in vacuo. Boc deprotection was carried out by addition of HCl (138 µL, 0.553 mmol, 4 M in dioxane) to the crude reaction mixture in 300 µL dioxane. Stirring at 50° C. for 24 h followed by concentration in vacuo yielded the title compound as its HCl salt (57 mg) as a white solid (10:1 regioisomeric mixture). ESI-MS m/z [M+H]+ 274.00.

Preparation 9 4-((3-fluorophenyl)sulfonyl)piperidine

A mixture of tert-butyl 4-((methylsulfonyl)oxy)piperidine-1-carboxylate (1.0 g, 3.58 mmol), K2CO3 (0.742 g, 5.37 mmol), and 3-fluorobenzenethiol (0.363 mL, 4.30 mmol) in ACN (7.5 mL) was stirred at 23° C. for 5 min. The reaction mixture was stirred at 80° C. for 17 h, cooled to 23° C. and partitioned between EtOAc and water. The layers were separated, the organic phase was washed with brine, dried over Na2SO4, filtered, rinsed with EtOAc, and dried in vacuo gave tert-butyl 4-((3-fluorophenyl)thio)piperidine-1-carboxylate (1.115 g, 100%) as a yellow oil. ESI-MS m/z [M+H]+ 255.9.

A mixture of basic alumina (3.0 g, 29.4 mmol) in water (0.6 mL) was stirred at 23° C. for 5 min. Next, ACN (12 mL) was added followed by a solution of tert-butyl 4-((3-fluorophenyl)thio)piperidine-1-carboxylate (1.115 g, 3.58 mmol) in CHCl3 (8 mL). Next, Oxone® (6.60 g, 10.74 mmol) was added and the reaction mixture was stirred at 60° C. for 19 h. The reaction mixture was cooled to 23° C., filtered, rinsed with CHCl3, and the filtrate was washed with water (10 mL). The organic layer was dried over Na2SO4, filtered, rinsed with CHCl3, and dried in vacuo. The crude residue was dissolved in toluene (5 mL) and purified via medium pressure chromatography using a gradient of 10% to 100% EtOAc with 0.1% triethylamine in heptane on a 80 g silica gel column (Single Step™) gave tert-butyl 4-((3-fluorophenyl)sulfonyl)piperidine-1-carboxylate (0.769 g, 62.5%) as a white solid. ESI-MS m/z [M+Na]+ 365.9.

To a solution of tert-butyl 4-((3-fluorophenyl)sulfonyl)piperidine-1-carboxylate (756 mg, 2.201 mmol) in dioxane (5.0 mL) was added HCl (4 M in dioxane, 5.50 mL, 22.01 mmol) at 23° C. The reaction was stirred at 23° C. for 21 h to furnish a white suspension. The resulting solid was filtered, rinsed with dioxane and dried in vacuo to give the title compound as its HCl salt (582.6 mg, 95%) as a white solid. ESI-MS m/z [M+H]+ 243.9.

Preparation 10
4-((3-methoxyphenyl)sulfonyl)piperidine

The title compound as its HCl salt was prepared in a similar manner to Preparation 9, with the exception that additional chloroform was used in place of ACN in the second step. ESI-MS m/z [M+H]+ 255.9.

Preparation 10
4-((4-fluorophenyl)sulfonyl)piperidine

A mixture of tert-butyl 4-((methylsulfonyl)oxy)piperidine-1-carboxylate (1.42 g, 5.08 mmol), 4-fluorobenzenethiol (0.663 ml, 6.10 mmol) and K2CO3 (1.054 g, 7.62 mmol) in ACN (12.71 mL) was stirred at 85° C. overnight. The reaction mixture was filtered by suction and the solvent removed gave tert-butyl 4-((4-fluorophenyl)thio)piperidine-1-carboxylate (1.5 g, 95%) as a white solid.

A solution of tert-butyl 4-((4-fluorophenyl)thio)piperidine-1-carboxylate (1.5 g) in water (16.06 mL) and MeOH (16.06 mL) was treated with Oxone® (5.92 g, 9.63 mmol) at room temperature and the resulting reaction mixture was stirred for 6 h. The solution was filtered by suction and the solvent removed gave tert-butyl 4-((4-fluorophenyl)sulfonyl)piperidine-1-carboxylate (1.6 g, 4.66 mmol, 97% yield) as a white solid.

A solution of tert-butyl 4-((4-fluorophenyl)sulfonyl)piperidine-1-carboxylate (32.7 mg, 0.095 mmol) in dioxane (238 μL) at room temperature was treated with HCl (4 M in dioxane, 190 μL, 0.762 mmol) and the resulting reaction mixture was stirred for 4 h. The solvent was removed to give the title compound as its HCl salt (25 mg, 94%) as a white solid. ESI-MS m/z [M+H]+ 243.95.

Preparation 11 1-(2,4-difluorobenzyl)piperazine

A mixture of piperazine (26.5 g, 308 mmol) in THF (350 mL) was heated to 70° C. and 1-(chloromethyl)-2,4-difluorobenzene (5 g, 30.8 mmol) was added. The suspension was heated at 70° C. overnight. The solid (piperazine) was filtered off, and the solvent was removed under reduced pressure. The residue was partitioned between EtOAc and water. The organic layer was dried and concentrated to give the title compound (6 g, 92%). ESI-MS m/z [M+H]+ 213.04.

Preparation 12
4-(2-fluoro-4-methoxyphenoxy)piperidine

A solution of tert-butyl 4-hydroxypiperidine-1-carboxylate (2.496 g, 12.03 mmol) in THF (33.4 mL) at room temperature was treated with 2-fluoro-4-methoxyphenol (1.181 mL, 10.03 mmol) and triphenylphosphine (3.16 g, 12.03 mmol). The reaction mixture was cooled to 0° C. and DEAD (40 wt % in toluene, 5.95 mL, 15.04 mmol) was added dropwise via syringe. The resulting reaction mixture was stirred at 65° C. for 5 h, then at room temperature overnight. Flash silica gel chromatography using a gradient of 10% to 100% EtOAc in hexanes gave tert-butyl 4-(2-fluoro-4-methoxyphenoxy)piperidine-1-carboxylate (2.78 g, 85%) as a light yellow oil. ESI-MS m/z [M+Na]+ 348.2.

A solution of tert-butyl 4-(2-fluoro-4-methoxyphenoxy)piperidine-1-carboxylate (2.78 g, 8.54 mmol) in dioxane (21.36 mL) was treated with HCl (4 M in dioxane, 21.36 mL, 85 mmol) at room temperature and the resulting reaction mixture stirred overnight. Flash silica gel chromatography using a gradient of 5% to 30% MeOH in DCM gave the title compound as its HCl salt (1.7 g, 76%) as a white solid. ESI-MS m/z [M+H]+ 226.20.

Preparation 13
4-(4-chloro-2-fluorophenoxy)piperidine

To a solution of tert-butyl 4-hydroxypiperidine-1-carboxylate (250 mg, 1.242 mmol) in THF (4.14 mL) was added 4-chloro-2-fluorophenol (0.15 mL, 1.366 mmol) and triphenylphosphine (391 mg, 1.491 mmol). The mixture was cooled to 0° C. and DEAD (0.81 mL, 2.050 mmol) (40% wt in toluene) was added dropwise. The mixture was heated at 65° C. for 15 h. The material was concentrated and purified via flash column chromatography (0-100% EtOAc in hexanes) to afford tert-butyl 4-(4-chloro-2-fluorophenoxy)piperidine-1-carboxylate (270 mg, 65%). ESI-MS m/z [M+H]+ 330.1.

To a solution of tert-butyl 4-(4-chloro-2-fluorophenoxy)piperidine-1-carboxylate (270 mg, 0.819 mmol) in dioxane (2.73 mL) was added HCl (4N in dioxane, 1.0 mL, 4.09 mmol). The mixture was stirred at 40° C. for 1.5 h and then concentrated to afford the HCl salt of the title compound (200 mg, 92%) as a white solid. ESI-MS m/z [M+H]+ 230.1.

Preparation 14 5-chloro-6-(cyclopropylamino)pyrazine-2,3-dicarbonitrile

To a solution of 5,6-dichloropyrazine-2,3-dicarbonitrile (10.48 g, 52.7 mmol) in THF (263 ml) at 0° C. was added cyclopropanamine (4.06 mL, 57.9 mmol). The resulting bright yellow reaction mixture was allowed to warm up slowly to 23° C. and stirred overnight. The reaction mixture was poured over water and extracted with EtOAc (3×250 mL). The organic layers were combined, dried over anhydrous MgSO4, filtered and the solvent was removed in vacuo. The crude product was purified by flash column chromatography (10-100% EtOAc in heptane) to afford the title compound (5.9 g, 51.0%) as a yellow solid. ESI-MS m/z [M+H]+ 220.0.

Preparation 15 5-chloro-6-(isopropylamino)pyrazine-2,3-dicarbonitrile

The title compound was prepared and purified in a manner similar to the preparation 14 using isopropylamine in place of cyclopropanamine. The crude material was purified by flash column chromatography (10-100% EtOAc in heptane) to give the title compound (72% yield). ESI-MS m/z [M+H]+ 222.0.

Preparation 16 methyl 5,6-dichloropyrazine-2-carboxylate

A solution of methyl 6-bromo-5-hydroxypyrazine-2-carboxylate (3 g, 12.87 mmol) and POCl3 (40 mL) was heated under reflux for 3 h and subsequently quenched with ice. The mixture was extracted with DCM and the organic layers were combined, concentrated and purified via flash chromatography (0-100% EtOAc in heptane) to afford the title compound (2.0 g, 75%). ESI-MS m/z [M+H]+ 208.0.

Preparation 17 methyl 6-chloro-5-(isopropylamino)pyrazine-2-carboxylate

A solution of methyl 5,6-dichloropyrazine-2-carboxylate (5.75 g, 27.8 mmol) and propan-2-amine (11.83 mL, 139 mmol) in dioxane (185 mL) was stirred at 23° C. for 2 h. The mixture was poured into water and brine, then extracted with EtOAc (1×100 mL) and DCM (2×100 mL). The organic layers were combined, dried with anhydrous MgSO4, filtered and the solvent was removed to afford the crude title compound (5.79 g, 91%) as a brown solid. ESI-MS m/z [M+H]+ 230.9.

Preparation 18 methyl 6-chloro-5-(cyclopropylamino)pyrazine-2-carboxylate

The title compound was prepared and purified in a manner similar to the preparation of 17 using cyclopropanamine in place of isopropanamine. Removal of the solvent gave the crude title compound (88% yield) as a white solid. ESI-MS m/z [M+H]+ 228.1.

Preparation 19
6-chloro-5-(isopropylamino)pyrazine-2-carboxylic acid

To a 50 mL RB flask with a stir bar was added methyl 6-chloro-5-(isopropylamino)pyrazine-2-carboxylate (2.0 g, 8.71 mmol) in dioxane (50 mL) and 1N sodium hydroxide (43.5 mL, 43.5 mmol). The reaction mixture was stirred at 23° C. for 2 h and concentrated to furnish a yellow solid. The crude material was triturated with acetonitrile (100 mL) and concentrated HCl was added to adjust pH=3. The resulting white precipitate was collected by filtration as the title compound (2.2 g, 100%). 1H NMR (500 MHz, DMSO-d6) δ ppm 1.23 (d, J=6.35 Hz, 6H), 2.51 (dt, J=3.54, 1.89 Hz, 3H), 4.30 (dt, J=8.05, 6.47 Hz, 1H), 7.46 (d, J=8.30 Hz, 1H), 8.60 (s, 1H); ESI-MS m/z [M+H]+ 216.5.

Preparation of 20 6-chloro-5-(isopropylamino)-N,N-dimethylpyrazine-2-carboxamide Combined 6-chloro-5-(isopropylamino)pyrazine-2-carboxylic acid (1.3 g, 6.03 mmol), dimethylamine hydrochloride (0.541 g, 6.63 mmol), HATU (2.292 g, 6.03 mmol) and DIPEA (4.21 mL, 24.11 mmol) in DMF (50 mL) under nitrogen. The solution was stirred at 23° C. for 2 h, quenched with brine (100 mL) and extracted with ethyl acetate (100 mL×2). The organic layers were separated, dried with anhydrous sodium sulfate, filtered and concentrated. Purification by flash column chromatography (30% EtOAc in heptane) afforded the title compound (0.9 g, 61.5%); ESI-MS m/z [M+H]+ 243.4.

Preparation 21 6-chloro-5-(isopropylamino)-N-methylpyrazine-2-carboxamide

The title compound was prepared and purified in a manner similar to the preparation of 20 using methylamine hydrochloride in place of dimethylamine hydrochloride. Purification by flash column chromatography (30% EtOAc in heptane) afforded the title compound (64% yield) as a light yellow solid. ESI-MS m/z [M+H]+ 229.5

Preparation 22
6-chloro-5-(isopropylamino)pyrazine-2-carbonitrile

To a solution of methyl 6-chloro-5-(isopropylamino)pyrazine-2-carboxylate (530 mg, 2.308 mmol) in MeOH (11.5 mL) was added NH4OH (21.0 mL, 178 mmol) at 23° C. The resulting reaction mixture was heated at 80° C. for 1 h. After the solvent was removed, the residue was purified by flash column chromatography (50% EtOAc in heptane) to afford 6-chloro-5-(isopropylamino)pyrazine-2-carboxamide (326.5 mg, 66%) as a yellow solid. ESI-MS m/z [M+H]+ 215.0.

A solution of 6-chloro-5-(isopropylamino)pyrazine-2-carboxamide (326 mg, 1.519 mmol) and TEA (1.69 mL, 12.15 mmol) in DCM (7.59 mL) was treated with trifluoroacetic anhydride (0.858 mL, 6.07 mmol) dropwise via a syringe at 23° C. and the resulting orange reaction mixture was stirred for 3 h. After the solvent was removed, the residue was purified by flash column chromatography (5-25% EtOAc in heptane) to afford the title compound (300 mg, 100%) as a yellow solid. ESI-MS m/z [M+H]+ 197.0.

Preparation 23 6-chloro-5-(cyclopropylamino)pyrazine-2-carbonitrile

The title compound was prepared and purified in a manner similar to the preparation of 22 using methyl 6-chloro-5-(cyclopropylamino)pyrazine-2-carboxylate in place of methyl 6-chloro-5-(isopropylamino)pyrazine-2-carboxylate. Purification by flash column chromatography (5-50% EtOAc in heptane) afforded the title compound (85% yield) as a white solid. ESI-MS m/z [M+H]+ 195.1.

Preparation 24 6-chloro-5-(4-(2,4-difluorophenoxy)piperidin-1-yl)-N,N-dimethylpyrazine-2-carboxamide A mixture of methyl 5,6-dichloropyrazine-2-carboxylate (400 mg, 1.932 mmol), cesium carbonate (1259 mg, 3.86 mmol) and 4-(2,4-difluorophenoxy)piperidine hydrochloride (386 mg, 1.546 mmol) in dioxane (20 mL) was heated at 120° C. for 1 h. After removal of solvent, the residue was purified by flash column chromatography (10-50% EtOAc in hexane) to methyl 6-chloro-5-(4-(2,4-difluorophenoxy)piperidin-1-yl)pyrazine-2-carboxylate (451.4 mg, 60.9%). ESI-MS m/z [M+H]+ 384.0.

To a solution of methyl 6-chloro-5-(4-(2,4-difluorophenoxy) piperidin-1-yl)pyrazine-2-carboxylate (451.4 mg, 1.176 mmol) in MeOH (10 mL) was added a solution of 1N NaOH (3.53 mL, 3.53 mmol) at 23° C. The reaction mixture was stirred at this temperature for 2 h. MeOH was removed in vacuo, then the solution was acidified with 1N HCl to pH=3. The mixture was extracted with EtOAc (10 mL×3), and the organic layers were dried over anhydrous Na2SO4, filtered and concentrated to give crude 6-chloro-5-(4-(2,4-difluorophenoxy)piperidin-1-yl)pyrazine-2-carboxylic acid (600 mg), which was used without further purification. ESI-MS m/z [M+H]+ 370.0.

A solution of 6-chloro-5-(4-(2,4-difluorophenoxy)piperidin-1-yl)pyrazine-2-carboxylic acid (600 mg, 1.62 mmol), dimethylamine hydrochloride (265 mg, 3.25 mmol), HATU (926 mg, 2.43 mmol) and DIPEA (1.134 ml, 6.49 mmol) in DMF (10.0 mL) under nitrogen was stirred at 23° C. for 2 h. The solvent was removed in vacuo, then the residue was dissolved in DCM, washed with H2O, dried over anhydrous Na2SO4 and filtered. Removal of the solvent in vacuo afforded the crude title compound (700 mg), which was used without further purification. ESI-MS m/z [M+H]+ 397.0.

Preparation 25 6-chloro-5-(4-(2,4-difluorophenoxy) piperidin-1-yl)pyrazine-2-carbonitrile A mixture of methyl 5,6-dichloropyrazine-2-carboxylate (500 mg, 2.415 mmol), 4-(2,4-difluorophenoxy)piperidine hydrochloride (680 mg, 2.72 mmol) and TEA (1.010 mL, 7.25 mmol) in DCM (20 mL) was heated at 120° C. for 3 h. The mixture was poured into water and extracted with EtOAc. The organic layer was concentrated to afford the crude methyl 6-chloro-5-(4-(2,4-difluorophenoxy)piperidin-1-yl)pyrazine-2-carboxylate (950 mg, 102%), which was used directly in next step without further purification. ESI-MS m/z [M+H]+ 383.8.

A mixture of methyl 6-chloro-5-(4-(2,4-difluorophenoxy)piperidin-1-yl)pyrazine-2-carboxylate (800 mg, 2.085 mmol) and NH4OH (20 mL, 154 mmol) in MeOH (20 mL) was heated at 90° C. for 16 h. The mixture was poured into water and extracted with EtOAc. The organic layer was concentrated to give the crude 6-chloro-5-(4-(2,4-difluorophenoxy)piperidin-1-yl)pyrazine-2-carboxamide (650 mg, 85%).

To a solution of 6-chloro-5-(4-(2,4-difluorophenoxy)piperidin-1-yl)pyrazine-2-carboxamide (250 mg, 0.678 mmol) and TEA (0.425 mL, 3.05 mmol) in DCM (15 mL) was added TFAA (0.192 mL, 1.356 mmol) dropwise at 0° C. Then the reaction solution was allowed to warm to 23° C. for 2 h. The mixture was poured into water and extracted with DCM. The organic layer was concentrated in vacuo to the crude title compound (220 mg, 93%). ESI-MS m/z [M+H]+ 350.8.

Preparation 26 6-chloro-5-(4-(4-chloro-2-fluorophenoxy)piperidin-1-yl)pyrazine-2-carbonitrile The title compound was prepared and purified in a manner similar to the preparation of 25 using 5,6-dichloropyrazine-2-carboxylate and 4-(4-chloro-2-fluorophenoxy)piperidine hydrochloride as the reaction substrates. The crude product was purified by flash column chromatography (20% EtOAc in heptane) to afford the titled compound (66.7% yield) as a yellow oil. ESI-MS m/z [M+H]+ 368.8.

Preparation 27 6-chloro-5-(4-((2,4-difluorophenyl)fluoromethyl)piperidin-1-yl)pyrazine-2-carbonitrile The title compound was prepared and purified in a manner similar to the preparation of 25 using 5,6-dichloropyrazine-2-carboxylate and 4-((2,4-difluorophenyl)fluoromethyl)piperidine hydrochloride as the reaction substrates to give 6-chloro-5-(4-((2,4-difluorophenyl)fluoromethyl)piperidin-1-yl)pyrazine-2-carbonitrile as its free base (30% yield over 3 steps).

Preparation 28 and 29 (S)-6-chloro-5-(4-((2,4-difluorophenyl)fluoromethyl)piperidin-1-yl)pyrazine-2-carbonitrile and (R)-6-chloro-5-(4-((2,4-difluorophenyl)fluoromethyl)piperidin-1-yl)pyrazine-2-carbonitrile Racemic 6-chloro-5-(4-((2,4-difluorophenyl)fluoromethyl)piperidin-1-yl)pyrazine-2-carbonitrile (240 mg, 0.654 mmol) from the above step was separated by chiral SFC separation to give (S)-6-chloro-5-(4-((2,4-difluorophenyl)fluoromethyl)piperidin-1-yl)pyrazine-2-carbonitrile (120 mg, 50.0%) and (R)-6-chloro-5-(4-((2,4-difluorophenyl)fluoromethyl)piperidin-1-yl)pyrazine-2-carbonitrile (100 mg, 41.7%).

Preparation of 30 3,6-dichloro-5-(isopropylamino)pyrazine-2-carbonitrile

To a solution of 3,5,6-trichloropyrazine-2-carbonitrile (5 g, 23.99 mmol) in dioxane (20 mL) at 0° C. under nitrogen was added propan-2-amine (4.09 mL, 48.0 mmol). The reaction solution was stirred at 23° C. for 4 h, then quenched with brine (300 mL) and extracted with ethyl acetate (2×200 mL). The organic layers were combined, dried over anhydrous MgSO4, filtered and concentrated. The residue was purified via flash column chromatography (5-30% EtOAc in heptane) to afford the title compound (5 g, 90%). 1H NMR (500 MHz, DMSO-d6) δ ppm 1.23 (d, J=6.83 Hz, 6H) 4.22 (dt, J=8.05, 6.47 Hz, 1H) 8.27 (d, J=7.81 Hz, 1H); ESI-MS m/z [M+H]+ 231.0.

Example 1 5-(cyclopropylamino)-6-(4-(2,4-difluorobenzyl)piperazin-1-yl)pyrazine-2,3-dicarbonitrile

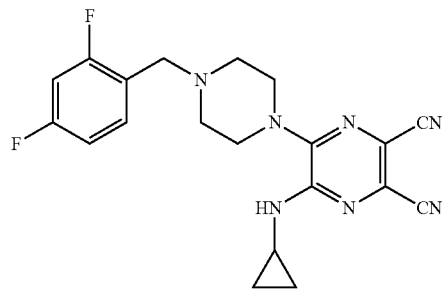 [SMILES: N#Cc1nc(NC2CC2)c(N2CCN(Cc3ccc(F)cc3F)CC2)nc1C#N]

A solution of 1-(2,4-difluorobenzyl)piperazine hydrochloride (400 mg, 1.608 mmol), 5-chloro-6-(cyclopropylamino)pyrazine-2,3-dicarbonitrile (353 mg, 1.608 mmol) and DIPEA (702 μL, 4.02 mmol) in DCM (16.1 mL) was stirred at 23° C. for 4 h. After the solvent was removed in vacuo, the crude product was purified by flash column chromatography (0-10% MeOH in DCM) to afford the title compound (456 mg, 71.7%) as a yellow solid. ESI-MS m/z [M+H]+ 396.0.

Example 2 5-(4-(2,4-difluorophenoxy)piperidin-1-yl)-6-(isopropylamino)pyrazine-2,3-dicarbonitrile

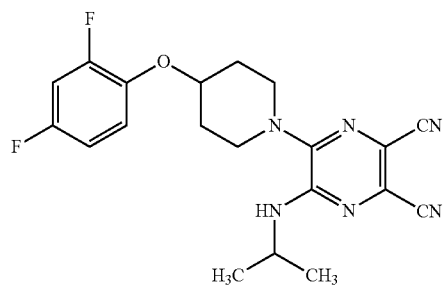 [SMILES: CC(C)Nc1nc(C#N)c(C#N)nc1N1CCC(Oc2ccc(F)cc2F)CC1]

The title compound was prepared and purified in a manner similar to Example 1 using 4-(2,4-difluorophenoxy)piperidine hydrochloride and 5-chloro-6-(isopropylamino)pyrazine-2,3-dicarbonitrile as the reaction substrates. The solvent was removed in vacuo to afford the crude product (99% yield), which was used without further purification.

Example 3: 5-(4-(5-chloro-2-fluorobenzoyl)piperidin-1-yl)-6-(isopropylamino)pyrazine-2,3-dicarbonitrile

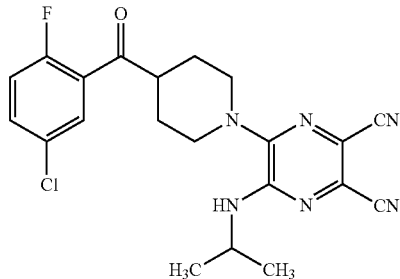 [SMILES: CC(C)Nc1nc(C#N)c(C#N)nc1N1CCC(C(=O)c2cc(Cl)ccc2F)CC1]

The title compound was prepared and purified in a manner similar to the preparation 1 using (5-chloro-2-fluorophenyl)(piperidin-4-yl)methanone hydrochloride and 5-chloro-6-(isopropylamino)pyrazine-2,3-dicarbonitrile as the reaction substrates. The solvent was removed in vacuo to give the crude title compound, which was used without further purification. ESI-MS m/z [M+H]+ 427.0.

Example 4 (R)-5-(4-((2,4-difluorophenyl)fluoromethyl)piperidin-1-yl)-6-(isopropylamino)pyrazine-2,3-dicarbonitrile

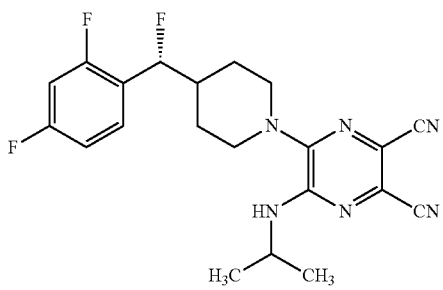 [SMILES: CC(C)Nc1nc(C#N)c(C#N)nc1N1CCC([C@@H](F)c2ccc(F)cc2F)CC1]

The title compound was prepared and purified in a manner similar to the preparation 1 using (R)-4-((2,4-difluorophenyl)fluoromethyl)piperidine hydrochloride and 5-chloro-6-(isopropylamino)pyrazine-2,3-dicarbonitrile as the reaction substrates. Removal of the solvent gave the crude title compound (96% yield) as a yellow solid, which was directly used in the next step without further purification. ESI-MS m/z [M+H]+ 415.0

Example 5 5-(4-(4-chloro-2-fluorophenoxy)piperidin-1-yl)-6-(isopropylamino)pyrazine-2,3-dicarbonitrile

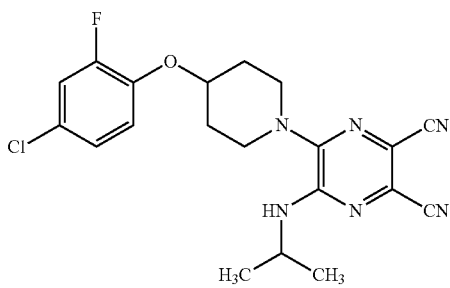 [SMILES: CC(C)Nc1nc(C#N)c(C#N)nc1N1CCC(Oc2ccc(Cl)cc2F)CC1]

To a solution of 5,6-dichloropyrazine-2,3-dicarbonitrile (150 mg, 0.754 mmol) in DCM (7.5 mL) at 0° C. was slowly added propan-2-amine (64.8 µL, 0.754 mmol), followed by DIPEA (395 µL, 2.261 mmol). The reaction solution was stirred at this temperature for 1 h, then 4-(4-chloro-2-fluorophenoxy)piperidine hydrochloride (281 mg, 1.055 mmol) was added. The reaction mixture was stirred 0° C. for 2 h and then warmed up to 23° C. for 2 h. After the solvent was removed in vacuo, the crude product was purified by flash column chromatography (0-60% EtOAc in heptanes) to afford its free base of the title compound (212 mg, 67.8%) as a yellow solid. 1H NMR (500 MHz, DMSO-d6) δ ppm 1.20 (d, J=6.35 Hz, 6H), 1.83 (dtd, J=12.63, 8.45, 8.45, 3.66 Hz, 2H), 2.05 (ddd, J=9.64, 6.71, 3.66 Hz, 2H), 3.23 (ddd, J=12.94, 9.03, 3.42 Hz, 2H), 3.54-3.63 (m, 2H), 4.15-4.25 (m, 1H), 4.70 (dt, J=7.81, 3.91 Hz, 1H), 7.22 (dq, J=8.85, 1.44 Hz, 1H), 7.29-7.36 (m, 1H), 7.39-7.49 (m, 2H), 8.10-8.10 (m, 1H) ESI-MS m/z [M+H]+ 414.85.

Example 6 5-(4-(4-chloro-2-fluorophenoxy)piperidin-1-yl)-3-cyano-6-(isopropylamino)pyrazine-2-carboxylic acid and 6-(4-(4-chloro-2-fluorophenoxy)piperidin-1-yl)-3-cyano-5-(isopropylamino)pyrazine-2-carboxylic acid

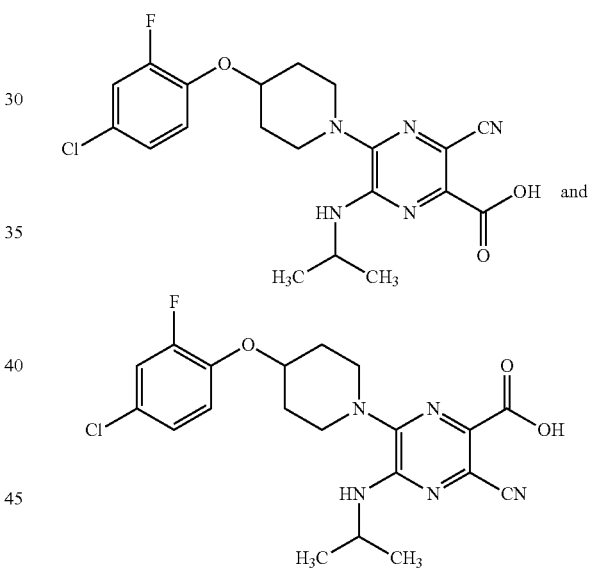

To a solution of 5-(4-(4-chloro-2-fluorophenoxy)piperidin-1-yl)-6-(isopropylamino)pyrazine-2,3-dicarbonitrile (150 mg, 0.362 mmol) in MeOH (1.0 mL) and dioxane (2.0 mL) was added a 2N solution of KOH (0.362 mL, 0.723 mmol). The reaction solution was stirred at 23° C. for 4 h. Then 3.0 mL 1N HCl solution was added to adjust the pH=1-2. The stirring was continued for 2 h. After the solvent mixture was removed in vacuo, the crude product was purified by flash column chromatography (10-60% EtOAc in heptane) to give a mixture of methyl 5-(4-(4-chloro-2-fluorophenoxy)piperidin-1-yl)-3-cyano-6-(isopropylamino)pyrazine-2-carboxylate and methyl 6-(4-(4-chloro-2-fluorophenoxy)piperidin-1-yl)-3-cyano-5-(isopropylamino)pyrazine-2-carboxylate (148 mg, 91%) as a yellow oil. [M+H]+ 447.9.

To a solution of the mixture of methyl 5-(4-(4-chloro-2-fluorophenoxy)piperidin-1-yl)-3-cyano-6-(isopropylamino)pyrazine-2-carboxylate and methyl 6-(4-(4-chloro-2-fluorophenoxy)piperidin-1-yl)-3-cyano-5-(isopropylamino)

pyrazine-2-carboxylate (132 mg, 0.295 mmol) in dioxane (2.0 mL) was added a 2N solution of KOH (184 μL, 0.368 mmol). The reaction mixture was stirred at 23° C. for 2 h. Then 1N HCl solution was used to adjust the pH=3-4. After the solvent mixture was removed in vacuo, the give a mixture of the title compounds (154 mg, 83 wt % of the desired product) which was dried under high vacuum for 5 h and used directly in the next step without further purification. ESI-MS m/z [M+H]+ 433.9.

Example 7 3-cyano-6-(cyclopropylamino)-5-(4-(2,4-difluorobenzyl)piperazin-1-yl)pyrazine-2-carb oxy c acid and 3-cyano-5-(cyclopropylamino)-6-(4-(2,4-difluorobenzyl)piperazin-1-yl)pyrazine-2-carboxylic acid

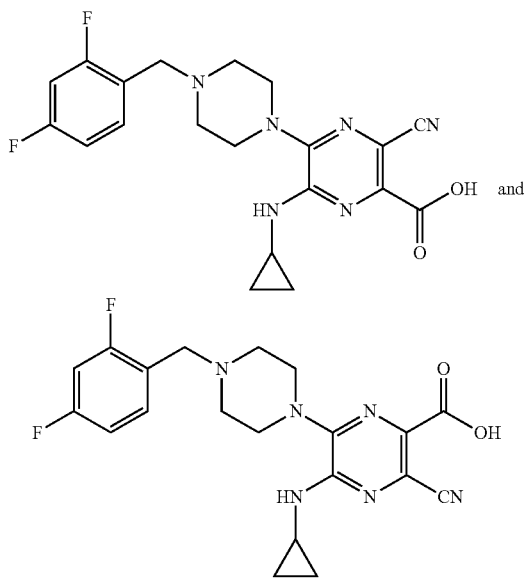

The title compound was prepared and purified in a manner similar to Example 6 using 5-(cyclopropylamino)-6-(4-(2,4-difluorobenzyl)piperazin-1-yl)pyrazine-2,3-dicarbonitrile in place of 5-(4-(4-chloro-2-fluorophenoxy)piperidin-1-yl)-6-(isopropylamino)pyrazine-2,3-dicarbonitrile. The title compound was obtained as a crude mixture of two regioisomers, which were used directly in the next step without further purification. ESI-MS m/z [M+H]+ 415.0.

Example 8 3-cyano-5-(4-(2,4-difluorophenoxy)piperidin-1-yl)-6-(isopropylamino)pyrazine-2-carboxylic acid and -cyano-6-(4-(2,4-difluorophenoxy)piperidin-1-yl)-5-(isopropylamino)pyrazine-2-carboxylic acid

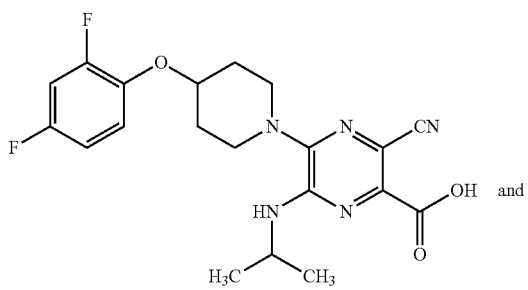

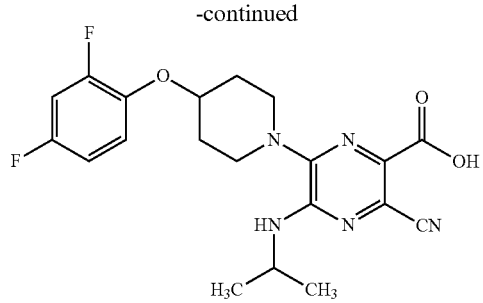

The title compound was prepared and purified in a manner similar to Example 6 using 5-(4-(2,4-difluorophenoxy)piperidin-1-yl)-6-(isopropylamino)pyrazine-2,3-dicarbonitrile in place of 5-(4-(4-chloro-2-fluorophenoxy)piperidin-1-yl)-6-(isopropylamino)pyrazine-2,3-dicarbonitrile. The title compound was obtained as a crude mixture of two regioisomers, which were used directly in the next step without further purification.

Example 9 5-(4-(5-chloro-2-fluorobenzoyl)piperidin-1-yl)-3-cyano-6-(isopropylamino)pyrazine-2-carboxylic acid and 6-(4-(5-chloro-2-fluorobenzoyl)piperidin-1-yl)-3-cyano-5-(isopropylamino)pyrazine-2-carboxylic acid

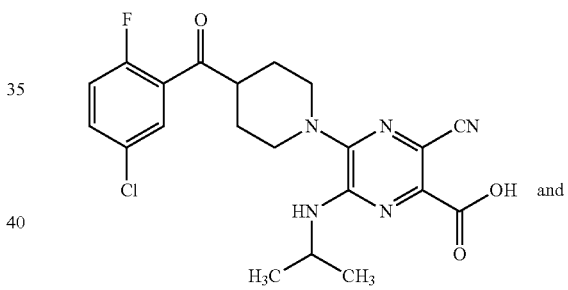

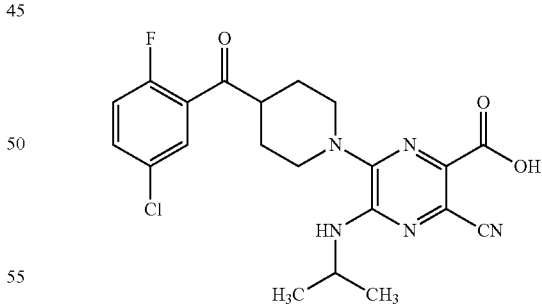

The title compound was prepared and purified in a manner similar to Example 6 using 5-(4-(5-chloro-2-fluorobenzoyl)piperidin-1-yl)-6-(isopropylamino)pyrazine-2,3-dicarbonitrile in place of 5-(4-(4-chloro-2-fluorophenoxy)piperidin-1-yl)-6-(isopropylamino)pyrazine-2,3-dicarbonitrile. The title compound was obtained as a crude mixture of two regioisomers, which were used directly in the next step without further purification. ESI-MS m/z [M+H]+ 446.0.

Example 10: (R)-3-cyano-5-(4-((2,4-difluorophenyl)
fluoromethyl)piperidin-1-yl)-6-(isopropylamino)
pyrazine-2-carboxylic acid and (R)-3-cyano-6-(4-
((2,4-difluorophenyl)fluoromethyl)piperidin-1-yl)-5-
(isopropylamino)pyrazine-2-carb oxy c acid

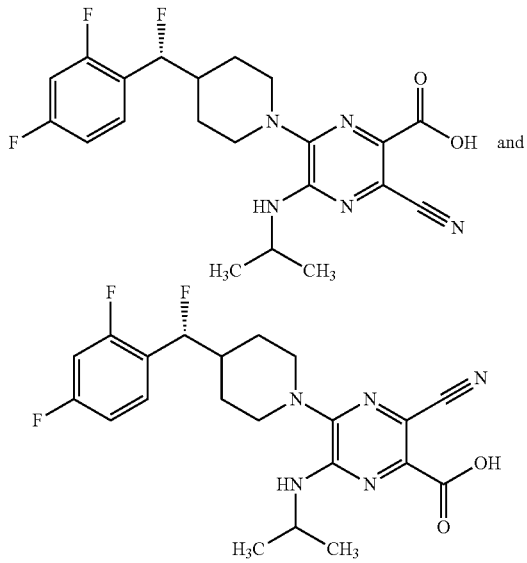

The title compound was prepared and purified in a manner similar to Example 6 using (R)-5-(4-((2,4-difluorophenyl)fluoromethyl)piperidin-1-yl)-6-(isopropylamino)pyrazine-2,3-dicarbonitrile in place of 5-(4-(4-chloro-2-fluorophenoxy)piperidin-1-yl)-6-(isopropylamino)pyrazine-2,3-dicarbonitrile. The title compound was obtained as a crude (1:1) mixture of two regioisomers (83% yield), which were used directly in the next step without further purification.

Example 11 6-(4-(2,4-difluorophenoxy)piperidin-1-yl)-5-(isopropylamino)-pyrazine-2-carboxylic acid

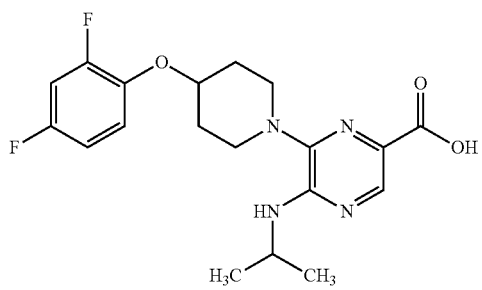 [SMILES: CC(C)Nc1ncc(C(=O)O)nc1N1CCC(Oc2ccc(F)cc2F)CC1]

To a stirred solution of methyl 6-chloro-5-(isopropylamino)pyrazine-2-carboxylate (300 mg, 1.306 mmol) and 4-(2,4-difluorophenoxy)piperidine (418 mg, 1.959 mmol) in DMSO (10 mL) was added TEA (0.55 mL, 3.92 mmol) dropwise. The resulting mixture was stirred at 120° C. for 5 h. The mixture was poured into water and extracted with EtOAc. The organic layer was concentrated to give methyl 6-(4-(2,4-difluorophenoxy)piperidin-1-yl)-5-(isopropylamino)pyrazine-2-carboxylate, which was used without further purification. ESI-MS m/z [M+H]+ 407.0.

To a solution of methyl 6-(4-(2,4-difluorophenoxy)piperidin-1-yl)-5-(isopropylamino)pyrazine-2-carboxylate (350 mg, 0.861 mmol) in MeOH (10 ml) was added 2N NaOH solution (20 mL). The resulting solution was stirred at 23° C. for 12 h. The reaction solution was concentrated in vacuo and then poured into water (10 mL), acidified with 2N HCl to adjust pH=3, and then extracted with EtOAc (2×20 mL). The combined organic layers were dried over anhydrous Na2SO4, filtered and concentrated to give the crude product. Purification by flash column chromatography (10-70% EtOAc in hexanes) gave the title compound (280 mg, 83%) as a yellow oil. ESI-MS m/z [M+H]+ 393.0.

Example 12 3-chloro-6-(4-(2,4-difluorophenoxy)
piperidin-1-yl)-5-(isopropylamino)pyrazine-2-carbonitrile

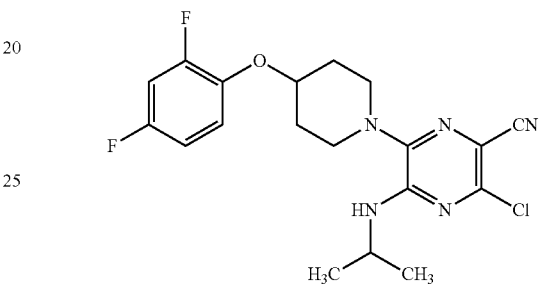

A mixture of 2,2'-bis(diphenylphosphino)-1,1'-binaphthalene (4.31 g, 6.92 mmol), diacetoxypalladium (0.777 g, 3.46 mmol), Cs2CO3 (16.92 g, 51.9 mmol), 4-(2,4-difluorophenoxy)piperidine hydrochloride (6.48 g, 26.0 mmol) and 3,6-dichloro-5-(isopropylamino)pyrazine-2-carbonitrile (4 g, 17.31 mmol) in toluene (10 mL) was heated in a microwave at 100° C. for 30 min. The reaction was duplicated with identical amounts and under the same conditions for 8 batches. The batches were combined, concentrated and purified via flash column chromatography (10-30% EtOA in heptane), followed by SFC Purification, to afford the title compound (900 mg, 13%) as a solid. 1H NMR (500 MHz, DMSO-d6) δ ppm 1.21 (d, J=6.35 Hz, 6H), 1.62-1.83 (m, 2H), 1.96-2.13 (m, 2H), 3.45-3.62, (m, 2H), 3.98 (ddd, J=13.30, 6.47, 3.66 Hz, 2H), 4.17 (dd, J=14.16, 6.35 Hz, 1H), 4.60 (dt, J=7.81, 3.91 Hz, 1H), 6.94-7.10 (m, 1H), 7.24-7.39 (m, 2H), 7.47 (d, J=7.81 Hz, 1H). ESI-MS m/z [M+H]+ 408.4.

Example 13 5-(4-(4-chloro-2-fluorophenoxy)piperidin-1-yl)-3-cyano-6-(isopropylamino)-N,N-dimethylpyrazine-2-carboxamide

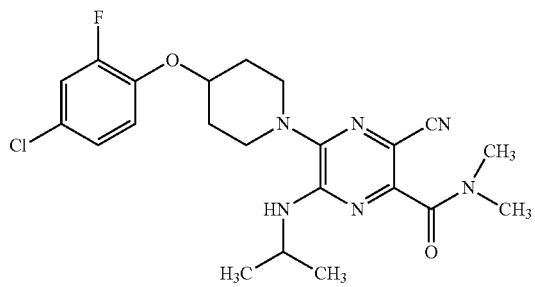 [SMILES: CC(C)Nc1nc(C(=O)N(C)C)c(C#N)nc1N1CCC(Oc2ccc(Cl)cc2F)CC1]

To a solution of a mixture of 5-(4-(4-chloro-2-fluorophenoxy)piperidin-1-yl)-3-cyano-6-(isopropylamino)pyrazine-2-carboxylic acid and 6-(4-(4-chloro-2-fluorophenoxy)piperidin-1-yl)-3-cyano-5-(isopropylamino)pyrazine-2-carboxylic acid (50 mg, 0.096 mmol in DMF (0.96 mL) was added HATU (36.4 mg, 0.096 mmol) and DIPEA (50.1 µl, 0.287 mmol) at 23° C. After the reaction solution was stirred for 10 min, dimethylamine (96 µL, 0.191 mmol) was added. Then the resulting solution was stirred at 23° C. for 2 h. The crude product was purified by HPLC using Method A, followed by a SFC purification, to afford its free base of the title compound (5.4 mg, 12%) as a yellow solid film. 1H NMR (500 MHz, methanol-d4) δ ppm 1.28 (d, J=6.35 Hz, 6H), 1.94-2.02 (m, 2H), 2.12-2.20 (m, 2H), 3.05 (s, 3H), 3.12-3.19 (m, 2H), 3.14 (s, 3H), 3.47-3.54 (m, 2H), 4.30 (spt, J=6.59 Hz, 1H), 4.59 (tt, J=7.38, 3.60 Hz, 1H), 7.10-7.15 (m, 1H), 7.16-7.23 (m, 2H) ESI-MS m/z [M+H]+ 460.9.

Example 14: 3-cyano-6-(cyclopropylamino)-5-(4-(2,4-difluorobenzyl)piperazin-1-yl)-N,N-dimethylpyrazine-2-carboxamide

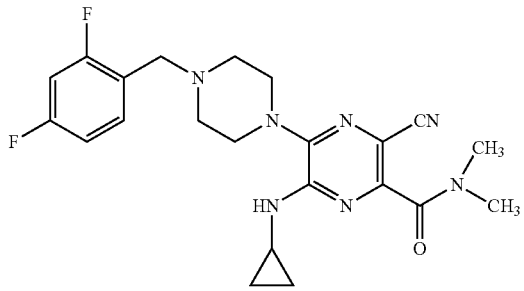 [SMILES: CN(C)C(=O)c1nc(NC2CC2)c(N2CCN(Cc3ccc(F)cc3F)CC2)nc1C#N]

The title compound was prepared and purified in a manner similar to Example 13 using a mixture of 3-cyano-6-(cyclopropylamino)-5-(4-(2,4-difluorobenzyl)piperazin-1-yl)pyrazine-2-carboxylic acid and -cyano-5-(cyclopropylamino)-6-(4-(2,4-difluorobenzyl)piperazin-1-yl)pyrazine-2-carboxylic acid as the substrates. The title compound was obtained as its free base as a white solid (11% yield). 1H NMR (500 MHz, methanol-d4) δ ppm 0.61-0.69 (m, 2H), 0.79-0.91 (m, 2H), 2.81 (tt, J=7.20, 3.78 Hz, 1H), 3.09 (s, 3H), 3.12-3.29 (m, 2H), 3.15 (s, 3H), 3.36-4.00 (m, 6H), 4.49 (s, 2H), 7.09-7.28 (m, 2H), 7.67 (td, J=8.54, 6.35 Hz, 1H) ESI-MS m/z [M+H]+ 442.0.

Example 15 and 16 3-cyano-5-(4-(2,4-difluorophenoxy)piperidin-1-yl)-6-(isopropylamino)-N,N-dimethylpyrazine-2-carboxamide and 3-cyano-6-(4-(2,4-difluorophenoxy)piperidin-1-yl)-5-(isopropylamino)-N,N-dimethylpyrazine-2-carboxamide

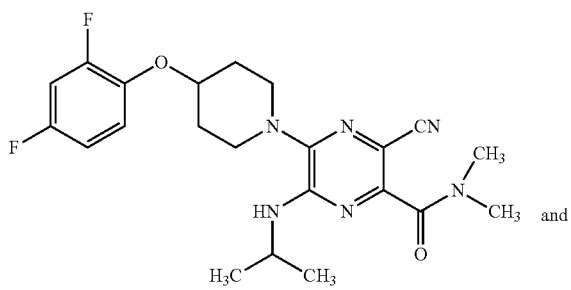

and

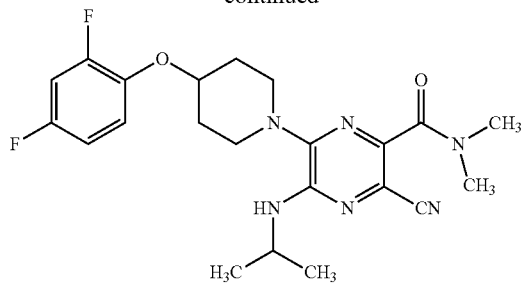

The title compound was prepared and purified in a manner similar to Example 13 using a mixture of 3-cyano-5-(4-(2,4-difluorophenoxy)piperidin-1-yl)-6-(isopropylamino)pyrazine-2-carboxylic acid and 3-cyano-6-(4-(2,4-difluorophenoxy)piperidin-1-yl)-5-(isopropylamino)pyrazine-2-carboxylic acid as the substrates. The crude material was purified by HPLC using Method A, followed by SFC separation, to afford 3-cyano-5-(4-(2,4-difluorophenoxy)piperidin-1-yl)-6-(isopropylamino)-N,N-dimethylpyrazine-2-carboxamide (14.5% yield) as an off-white solid. 1H NMR (500 MHz, methanol-d4) ppm 1.23-1.30 (m, 6H) 1.86-2.00 (m, 3H) 2.06-2.17 (m, 2H) 2.98-3.17 (m, 7H) 3.46-3.54 (m, 1H) 3.58-3.66 (m, 1H) 4.21-4.34 (m, 1H) 4.50 (td, J=7.44, 3.66 Hz, 1H) 6.83-6.90 (m, 1H) 6.95-7.03 (m, 1H) 7.14-7.22 (m, 1H); ESI-MS m/z [M+H]+ 445.0; and 3-cyano-6-(4-(2,4-difluorophenoxy)piperidin-1-yl)-5-(isopropylamino)-N,N-dimethylpyrazine-2-carboxamide (2.0% yield) as a white solid. 1H NMR (500 MHz, methanol-d4) δ ppm 1.27 (d, J=6.83 Hz, 6H), 1.83-2.00 (m, 2H), 2.03-2.19 (m, 2H), 3.02-3.18 (m, 6H), 3.27-3.35 (m, 2H), 3.49-3.70 (m, 2H), 4.25 (t, J=6.35 Hz, 1H), 4.46-4.56 (m, 1H), 6.77-6.93 (m, 1H), 6.98 (ddd, J=11.35, 8.42, 3.17 Hz, 1H) 7.17 (td, J=9.28, 5.37 Hz, 1H); ESI-MS m/z [M+H]+ 445.4.

Example 17 5-(4-(5-chloro-2-fluorobenzoyl)piperidin-1-yl)-3-cyano-6-(isopropylamino)-N,N-dimethylpyrazine-2-carboxamide

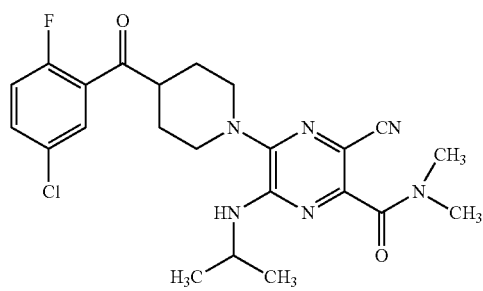 [SMILES: CC(C)Nc1nc(C(=O)N(C)C)c(C#N)nc1N1CCC(C(=O)c2cc(Cl)ccc2F)CC1]

The title compound was prepared and purified in a manner similar to Example 13 using a mixture of 5-(4-(5-chloro-2-fluorobenzoyl)piperidin-1-yl)-3-cyano-6-(isopropylamino)pyrazine-2-carboxylic acid and 6-(4-(5-chloro-2-fluorobenzoyl)piperidin-1-yl)-3-cyano-5-(isopropylamino)pyrazine-2-carboxylic acid as the substrates. The title compound was purified by HPLC using Method B to afford its TFA salt (44% yield) as an off-white solid. 1H NMR (500 MHz, methanol-d4) ppm 1.22-1.29 (m, 6H) 1.85-1.96 (m, 2H) 1.96-2.06 (m, 2H) 2.89-2.97 (m, 2H) 3.03 (s, 3H) 3.09-3.15 (m, 3H) 3.33-3.41 (m, 1H) 3.58-3.65 (m, 2H) 4.28 (t, J=6.35

Hz, 1H) 7.28 (dd, J=10.25, 8.79 Hz, 1H) 7.57-7.63 (m, 1H) 7.73-7.78 (m, 1H) ESI-MS m/z [M+H]+ 473.0.

Example 18: (R)-3-cyano-5-(4-((2,4-difluorophenyl)fluoromethyl)piperidin-1-yl)-N-(2-(dimethylamino)ethyl)-6-(isopropylamino)-N-methylpyrazine-2-carboxamide

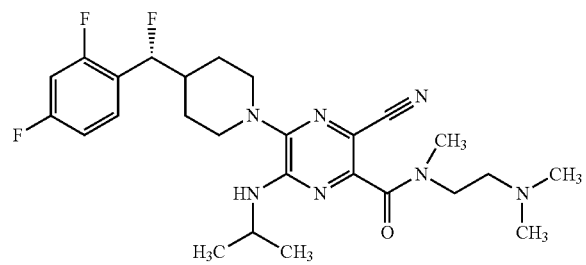 [SMILES: CC(C)Nc1nc(C(=O)N(C)CCN(C)C)c(C#N)nc1N1CCC([C@@H](F)c2ccc(F)cc2F)CC1]

The title compound was prepared and purified in a manner similar to Example 13 using a mixture of (R)-3-cyano-5-(4-((2,4-difluorophenyl)fluoromethyl)piperidin-1-yl)-6-(isopropylamino)pyrazine-2-carboxylic acid compound and (R)-3-cyano-6-(4-((2,4-difluorophenyl)fluoromethyl)piperidin-1-yl)-5-(isopropylamino)pyrazine-2-carboxylic acid (1:1), and N1,N1,N2-trimethylethane-1,2-diamine as the reaction substrates. Purification by flash column chromatography, eluting with 50:1 to 15:1 DCM:MeOH, followed by SFC purification, to give the title compound (17% yield) as an off-white solid. 1H NMR (500 MHz, CDCl3) δ ppm 1.27 (d, J=5.2 Hz, 6H), 1.57-1.60 (m, 2H), 3.57 (br. s., 8H), 4.48 (s, 2H), 4.66 (quin, J=6.59 Hz, 1H), 7.11-7.24 (m, 2H), 7.61 (s, 1H), 7.68 (td, J=8.54, 6.35 Hz, 1H), 8.83 (s, 1H); ESI-MS m/z [M+H]+ 518.1.

Example 19: 6-(4-(2,4-difluorophenoxy)piperidin-1-yl)-5-(isopropylamino)-N,N-dimethylpyrazine-2-carboxamide

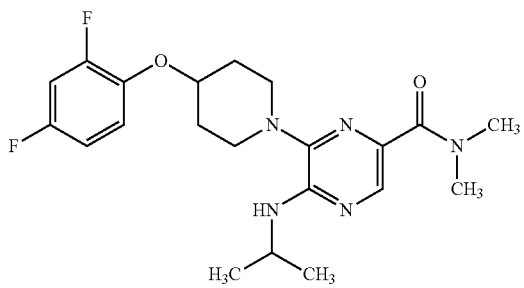 [SMILES: CC(C)Nc1ncc(C(=O)N(C)C)nc1N1CCC(Oc2ccc(F)cc2F)CC1]

A mixture of 6-chloro-5-(isopropylamino)-N,N-dimethylpyrazine-2-carboxamide (50 mg, 0.206 mmol), DIPEA (0.144 ml, 0.824 mmol) and 4-(2,4-difluorophenoxy)piperidine hydrochloride (103 mg, 0.412 mmol) in dioxane (2.0 mL) was heated at 180° C. in the microwave for 4 h. The mixture was purified by HPLC using Method A to afford the title compound as its TFA salt (10 mg, 12%) as a yellow film. 1H NMR (500 MHz, DMSO-d6) δ ppm 1.21 (d, J=6.35 Hz, 6H), 1.77-1.97 (m, 2H) 2.07 (br. s., 2H), 2.81-3.00 (m, 2H), 3.15 (d, J=19.53 Hz, 2H), 3.38 (m, 6H), 4.22 (d, J=14.40, 6.59 Hz, 1H), 4.54 (dt, J=7.93, 4.09 Hz, 1H), 6.11 (d, J=8.30 Hz, 1H), 6.93-7.08 (m, 1H), 7.21-7.43 (m, 2H), 8.01 (s, 1H); ESI-MS m/z [M+H]+ 420.4.

Example 20 6-(4-(5-chloro-2-fluorobenzoyl)piperidin-1-yl)-5-(isopropylamino)-N,N-dimethylpyrazine-2-carboxamide

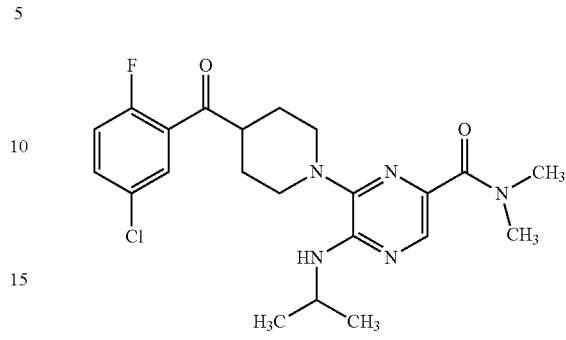

6-(4-((5-Chloro-2-fluorophenyl)(hydroxy)methyl)piperidin-1-yl)-5-(isopropylamino)-N,N-dimethylpyrazine-2-carboxamide was prepared and purified in a manner similar to Example 19 using (5-chloro-2-fluorophenyl)(piperidin-4-yl)methanol in place of 4-(2,4-difluorophenoxy)piperidine hydrochloride. Purification by HPLC using Method A to give 6-(4-((5-chloro-2-fluorophenyl)(hydroxy)methyl)piperidin-1-yl)-5-(isopropylamino)-N,N-dimethylpyrazine-2-carboxamide as its TFA salt (47 mg, 85%) as a white solid. 1H NMR (500 MHz, DMSO-d6) ppm 1.09-1.29 (m, 6H) 1.36 (d, J=12.69 Hz, 1H) 1.48-1.72 (m, 2H) 1.81 (d, J=12.20 Hz, 1H), 2.53-2.55 (m, 2H) 2.94 (s, 3H) 3.10 (s, 3H) 3.31-3.48 (m, 2H) 4.19 (dd, J=14.40, 6.59 Hz, 1H) 4.65 (d, J=6.35 Hz, 1H) 5.98 (d, J=8.30 Hz, 1H) 7.15-7.32 (m, 1H) 7.32-7.42 (m, 1H) 7.48 (dd, J=6.10, 2.69 Hz, 1H) 7.98 (s, 1H); ESI-MS m/z [M+H]+ 450.3.

To a solution of 6-(4-((5-chloro-2-fluorophenyl)(hydroxy)methyl)piperidin-1-yl)-5-(isopropylamino)-N,N-dimethylpyrazine-2-carboxamide (42 mg, 0.093 mmol) in DCM (5 mL) was added Dess-Martin Periodinane (99 mg, 0.233 mmol). The reaction solution was stirred at 23° C. for 2 h. The mixture was filtered and purified by HPLC using Method A twice to afford the title compound as its TFA salt (0.5 mg, 1.0%) as a clear film. 1H NMR (500 MHz, methanol-d4) δ ppm 1.29 (m, 6H), 1.93 (m, 2H) 2.02 (m, 2H), 2.65 (m, 2H), 3.16 (m, 2H), 3.33-3.34 (m, 6H), 4.33 (m, 1H), 4.61 (m, 1H), 7.26 (m, 1H), 7.29 (m, 1H), 7.74 (m, 2H), 8.07 (s, 1H); ESI-MS m/z [M+H]+ 450.3.

Example 21 (R)-6-(4-((2,4-difluorophenyl)fluoromethyl)piperidin-1-yl)-5-(isopropylamino)-N-methylpyrazine-2-carboxamide

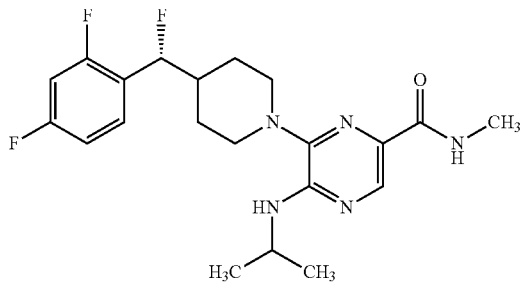 [SMILES: CNC(=O)c1cnc(NC(C)C)c(N2CCC([C@@H](F)c3ccc(F)cc3F)CC2)n1]

The title compound was prepared and purified in a manner similar to Example 19 using (R)-4-((2,4-difluorophenyl)

fluoromethyl)piperidine hydrochloride and 6-chloro-5-(isopropylamino)-N-methylpyrazine-2-carboxamide as the reaction substrates. The title compound was obtained as its TFA salt (11% yield) as a white solid. 1H NMR (500 MHz, DMSO-d6) δ ppm 1.20 (d, J=6.35 Hz, 6H), 1.34 (d, J=12.69 Hz, 1H), 1.49-1.78 (m, 2H), 1.93 (d, J=12.20 Hz, 1H), 2.09 (br. s., 1H), 2.60-2.76 (m, 2H), 2.77 (d, J=4.88 Hz, 3H), 3.22-3.55 (m, 2H) 4.20-4.24 (m, 1H) 5.45-5.68 (m, 1H), 6.13 (d, J=8.30 Hz, 1H), 7.20 (t, J=8.30 Hz, 1H), 7.34 (t, J=10.01 Hz, 1H), 7.51-7.65 (m, 1H), 7.94 (d, J=4.88 Hz, 1H), 8.21 (s, 1H); ESI-MS m/z [M+H]+ 422.2.

Example 22 (S)-6-(4-((2,4-difluorophenyl)fluoromethyl)piperidin-1-yl)-5-(isopropylamino)-N-methylpyrazine-2-carboxamide

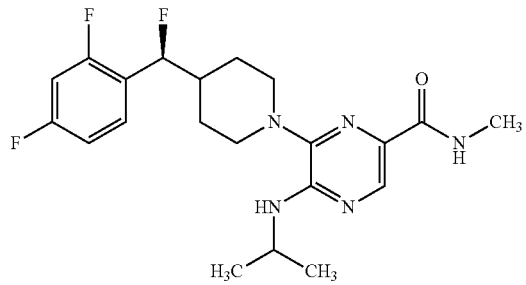 [SMILES: CNC(=O)c1cnc(NC(C)C)c(N2CCC([C@H](F)c3ccc(F)cc3F)CC2)n1]

The title compound was prepared and purified in a manner similar to Example 19 using (S)-4-((2,4-difluorophenyl)fluoromethyl)piperidine hydrochloride and 6-chloro-5-(isopropylamino)-N-methylpyrazine-2-carboxamide as the reaction substrates. The title compound was obtained as its TFA salt (14% yield) as a white solid. 1H NMR (500 MHz, DMSO-d6) ppm 1.20 (d, J=6.35 Hz, 6H), 1.34 (d, J=11.72 Hz, 1H), 1.49-1.78 (m, 2H), 1.93 (d, J=13.18 Hz, 1H), 2.09 (d, J=3.91 Hz, 1H), 2.57-2.66 (m, 2H), 2.76-2.77 (d, J=4.9 Hz, 3H), 3.42-3.45 (m, 2H), 4.19-4.26 (m, 1H), 5.42-5.69 (m, 1H), 6.12 (d, J=7.81 Hz, 1H), 7.11-7.27 (m, 1H), 7.29-7.40 (m, 1H), 7.51-7.65 (m, 1H), 7.94 (d, J=4.88 Hz, 1H), 8.21 (s, 1H); ESI-MS m/z [M+H]+ 422.2.

Example 23 6-(4-(2,4-difluorophenoxy)piperidin-1-yl)-N-(2-(dimethylamino)-ethyl)-5-(isopropylamino)-N-methylpyrazine-2-carboxamide

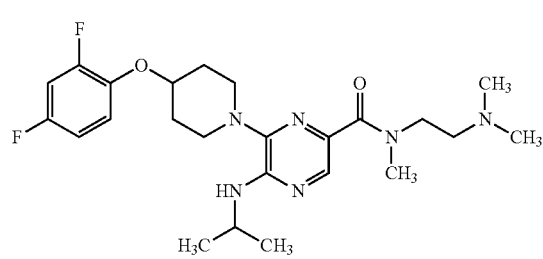 [SMILES: CC(C)Nc1ncc(C(=O)N(C)CCN(C)C)nc1N1CCC(Oc2ccc(F)cc2F)CC1]

To a solution of 6-(4-(2,4-difluorophenoxy)piperidin-1-yl)-5-(isopropylamino)pyrazine-2-carboxylic acid (65 mg, 0.166 mmol), N1,N1,N2-trimethylethane-1,2-diamine (16.93 mg, 0.166 mmol) and HATU (126 mg, 0.331 mmol) in THF (5 mL) was added DIPEA (0.02 mL, 0.13 mmol). The resulting solution was stirred at 23° C. for 1 h. The mixture was extracted with EtOAc (10 mL) and washed with water (10 mL) and brine (2×10 mL). The combined organic layers were dried over anhydrous Na2SO4, filtered and concentrated to give the crude product. Purification by flash column chromatography, eluting with 50:1 to 2:1 DCM/MeOH, gave the title compound (70 mg, 89%) as a white solid. 1H NMR (500 MHz, CDCl3) δ ppm 1.27 (d, J=5.2 Hz, 6H), 1.57-1.60 (m, 2H), 3.57 (br. s., 8H), 4.48 (s, 2H), 4.66 (quin, J=6.59 Hz, 1H), 7.11-7.24 (m, 2H), 7.61 (s, 1H), 7.68 (td, J=8.54, 6.35 Hz, 1H), 8.83 (s, 1H); ESI-MS m/z [M+H]+ 477.1.

Example 24: (6-(4-(2,4-difluorophenoxy)piperidin-1-yl)-5-(isopropylamino) pyrazin-2-yl)(3-fluoroazetidin-1-yl)methanone

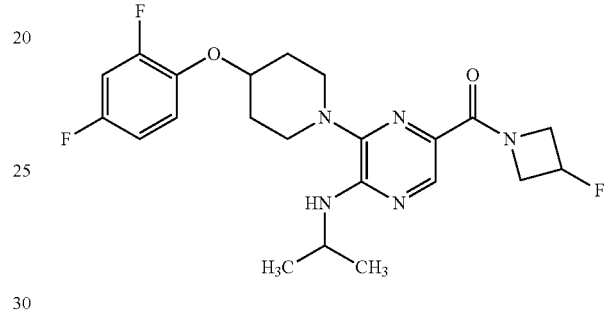

The title compound was prepared in a manner similar to Example 23 using 3-fluoroazetidine hydrochloride in place of N1,N1,N2-trimethylethane-1,2-diamine. Purification by HPLC using Method B afforded its TFA salt of the title compound (67.5% yield) as a pale yellow semisolid. 1H NMR (500 MHz, DMSO-d6) ppm 1.16-1.30 (m, 6H) 1.84-1.95 (m, 2H) 2.09 (br. s., 2H) 2.91 (d, J=9.28 Hz, 2H) 3.12-3.20 (m, 1H) 3.34 (br. s., 1H) 3.96-4.09 (m, 1H) 4.21-4.42 (m, 2H) 4.51-4.64 (m, 2H) 4.83-4.95 (m, 1H) 5.32-5.52 (m, 1H) 6.33 (d, J=8.30 Hz, 1H) 6.99-7.06 (m, 1H) 7.24-7.39 (m, 2H) 8.24-8.30 (m, 1H); ESI-MS m/z [M+H]+ 450.0.

Example 25 5-(4-(2,4-difluorophenoxy)piperidin-1-yl)-6-(isopropylamino)-N,N-dimethylpyrazine-2-carboxamide

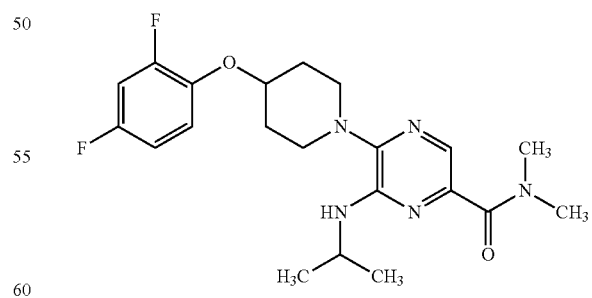

A solution of 6-chloro-5-(4-(2,4-difluorophenoxy)piperidin-1-yl)-N,N-dimethylpyrazine-2-carboxamide (300 mg, 0.756 mmol), propan-2-amine (89 mg, 1.512 mmol) and DIPEA (391 mg, 3.02 mmol) in dioxane (2.0 mL) was heated at 140° C. under microwave irradiation for 1 h. The reaction mixture was filtered and purified by HPLC using Method B to afford its TFA salt of the title compound (29 mg, 9.1%) as an off-white solid. 1H NMR (500 MHz, DMSO-d6) ppm 1.16-1.22 (m, 6H) 1.83-1.93 (m, 2H) 2.02-2.11 (m, 2H) 2.91-3.00 (m, 5H) 3.04 (s, 3H) 3.39 (d, J=3.91 Hz, 2H) 4.07-4.16 (m, 1H) 4.55 (tt, J=8.05, 3.91 Hz, 1H) 5.81 (d, J=7.81 Hz, 1H) 6.99-7.06 (m, 1H) 7.25-7.37 (m, 2H) 7.59-7.63 (m, 1H); ESI-MS m/z [M+H]+ 420.0.

Example 26: (R)-5-(cyclopropylamino)-6-(4-((2,4-difluorophenyl)fluoromethyl)piperidin-1-yl)pyrazine-2-carbonitrile

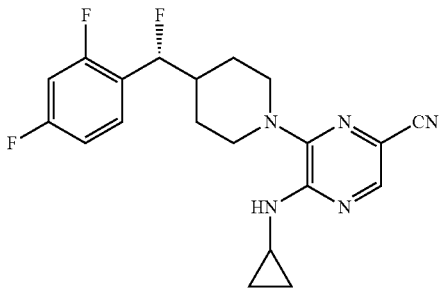 [SMILES: N#Cc1cnc(NC2CC2)c(N2CCC([C@@H](F)c3ccc(F)cc3F)CC2)n1]

A solution of 6-chloro-5-(cyclopropylamino)pyrazine-2-carbonitrile (2 mg, 10.28 μmol), (R)-4-((2,4-difluorophenyl)fluoromethyl)piperidine hydrochloride (41.1 mg, 0.155 mmol) and DIPEA (26.6 mg, 0.206 mmol) in dioxane (0.34 mL) was heated at 120° C. for 10 h. The mixture was purified by HPLC using Method A to afford its TFA salt of the title compound (40.6% yield) as a brown solid. 1H NMR (500 MHz, methanol-d4) δ ppm 0.67-0.70 (m, 2H), 0.88-0.92 (m, 2H), 1.43-1.45 (m, 1H), 1.42-1.74 (m, 2H), 1.99-2.06 (m, 1H), 2.08-2.13 (m, 1H), 2.70-2.80 (m, 3H), 3.32-3.60 (m, 2H), 5.48 (dd, J=42.2, 7.6 Hz, 2H), 6.99-7.08 (m, 2H), 7.49-7.54 (m, 1H), 8.08 (s, 1H); ESI-MS m/z [M+H]+ 388.3.

Example 27: 6-(4-(2,4-difluorophenoxy)piperidin-1-yl)-5-(isopropylamino)pyrazine-2-carbonitrile

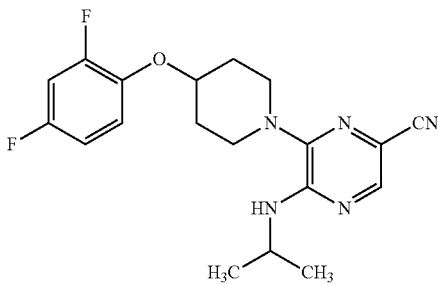 [SMILES: CC(C)Nc1ncc(C#N)nc1N1CCC(Oc2ccc(F)cc2F)CC1]

The title compound was prepared and purified in a manner similar to Example 26 using 6-chloro-5-(isopropylamino)pyrazine-2-carbonitrile and 4-(2,4-difluorophenoxy)piperidine hydrochloride as the reaction substrates. The title compound was purified by HPLC using Method A to afford its TFA salt (50.0% yield) as a white solid. 1H NMR (500 MHz, methanol-d4) δ ppm 1.27-1.33 (m, 6H), 1.97-2.05 (m, 2H), 2.13-2.22 (m, 2H), 3.17-3.24 (m, 2H), 3.45-3.51 (m, 2H), 4.42-4.45 (m, 1H), 4.50-4.53 (m, 1H), 6.91-7.01 (m, 1H), 7.10-7.15 (m, 1H), 7.21-7.30 (m, 1H), 8.15 (s, 1H); ESI-MS m/z [M+H]+ 374.3.

Example 28 5-(4-(2,4-difluorophenoxy)piperidin-1-yl)-6-(isopropylamino)pyrazine-2-carbonitrile

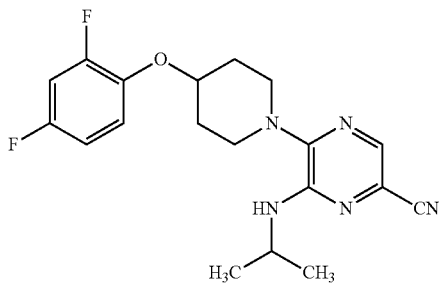 [SMILES: CC(C)Nc1nc(C#N)cnc1N1CCC(Oc2ccc(F)cc2F)CC1]

A mixture of 6-chloro-5-(4-(2,4-difluorophenoxy)piperidin-1-yl)pyrazine-2-carbonitrile (150 mg, 0.428 mmol), propan-2-amine (0.728 mL, 8.55 mmol) and TEA (0.596 mL, 4.28 mmol) in DMSO (5.0 mL) was heated at 80° C. for 16 h. The mixture was poured into water and extracted with EtOAc. The organic layer was concentrated and the crude product was purified by flash column chromatography (10-100% EtOAc in heptane) to afford the title compound (53.7 mg, 33.6%). 1H NMR (500 MHz, CDCl3) δ ppm 1.23 (d, J=6.4 Hz, 6H), 1.89-1.86 (m, 2H), 2.16-2.07 (m, 2H), 3.10-3.06 (m, 2H), 3.51-3.48 (m, 2H), 4.13-4.10 (m, 1H), 4.49-4.47 (m, 1H), 5.23 (d, J=7.2 Hz, 1H), 6.99-6.89 (m, 1H), 7.01-7.00 (m, 1H), 7.18-7.13 (m, 1H). ESI-MS m/z [M+H]+ 373.8.

Example 29 5-(4-(4-chloro-2-fluorophenoxy)piperidin-1-yl)-6-(cyclopropylamino)pyrazine-2-carbonitrile

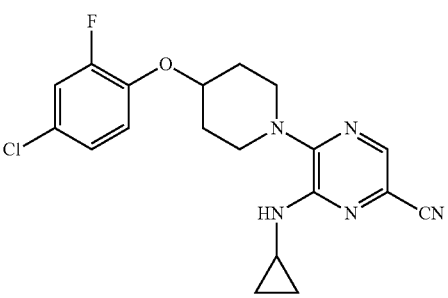 [SMILES: N#Cc1cnc(N2CCC(Oc3ccc(Cl)cc3F)CC2)c(NC2CC2)n1]

The title compound was prepared and purified in a manner similar to Example 28 using 6-chloro-5-(4-(4-chloro-2-fluorophenoxy)piperidin-1-yl)pyrazine-2-carbonitrile and cyclopropanamine as the reaction substrates. The title compound was obtained as its free base (52% yield) as a white solid. 1H NMR (500 MHz, CDCl3) δ ppm 0.53-0.56 (m, 2H) 0.86-0.91 (m, 2H) 1.94 (ddt, J=17.33, 7.44, 3.72, 3.72 Hz, 2H) 2.05-2.13 (m, 2H) 2.74-2.79 (m, 1H) 3.08-3.14 (m, 2H) 3.46-3.52 (m, 3H) 4.46 (tt, J=7.26, 3.48 Hz, 1H) 5.12 (br. s., 1H) 6.93-6.97 (m, 1H) 7.03-7.06 (m, 1H) 7.12 (dd, J=10.74, 2.44 Hz, 1H) 7.92 (s, 1H). ESI-MS m/z [M+H]+ 387.9.

Example 30 (S)-5-(4-((2,4-difluorophenyl)fluoromethyl)piperidin-1-yl)-6-(isopropylamino)pyrazine-2-carbonitrile

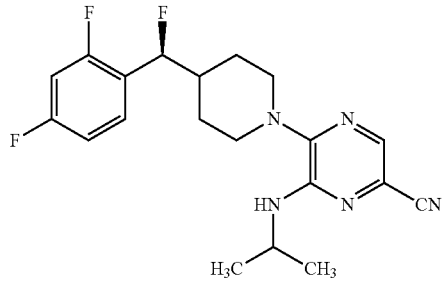 [SMILES: CC(C)Nc1nc(C#N)cnc1N1CCC([C@H](F)c2ccc(F)cc2F)CC1]

The title compound was prepared and purified in a manner similar to Example 28 using (S)-6-chloro-5-(4-((2,4-difluorophenyl)fluoromethyl)piperidin-1-yl)pyrazine-2-carbonitrile as the substrate in place of 6-chloro-5-(4-(2,4-difluorophenoxy)piperidin-1-yl)pyrazine-2-carbonitrile. The title compound was purified by HPLC to give its HCl salt (14.2% yield) as a white solid. 1H NMR (500 MHz, methanol-d4) δ ppm 1.25 (d, J=6.8 Hz, 6H), 1.46-1.44 (m, 1H), 1.67-1.61 (m, 2H), 1.98-1.96 (m, 1H), 2.03-2.01 (m, 1H), 2.82-2.74 (m, 2H), 3.76-3.70 (m, 1H), 4.18-4.15 (m, 1H), 5.50 (dd, J=48, 7.2 Hz, 1H), 7.06-6.98 (m, 2H), 7.51-7.47 (m, 1H), 7.79 (s, 1H). ESI-MS m/z [M+H]+ 389.9.

Example 31: (R)-5-(4-((2,4-difluorophenyl)fluoromethyl)piperidin-1-yl)-6-(isopropylamino)pyrazine-2-carbonitrile

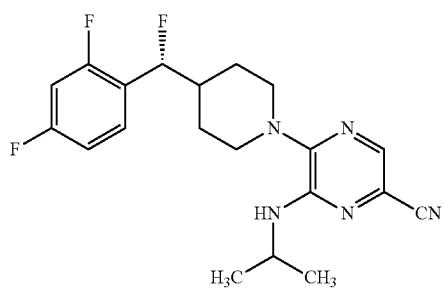

The title compound was prepared and purified in a manner similar to Example 28 using (R)-6-chloro-5-(4-((2,4-difluorophenyl)fluoromethyl)piperidin-1-yl)pyrazine-2-carbonitrile as the substrate in place of 6-chloro-5-(4-(2,4-difluorophenoxy)piperidin-1-yl)pyrazine-2-carbonitrile. The title compound was purified by HPLC to give its HCl salt (29.7% yield) as a white solid. 1H NMR (500 MHz, methanol-d4) δ ppm 1.25 (d, J=6.8 Hz, 6H), 1.46-1.44 (m, 1H), 1.67-1.61 (m, 2H), 1.98-1.96 (m, 1H), 2.03-2.01 (m, 1H), 2.82-2.74 (m, 2H), 3.76-3.70 (m, 1H), 4.18-4.15 (m, 1H), 5.50 (dd, J=48, 7.2 Hz, 1H), 7.06-6.98 (m, 2H), 7.51-7.47 (m, 1H), 7.79 (s, 1H). ESI-MS m/z [M+H]+ 389.9.

Example 32 6-(4-(2,4-difluorophenoxy)piperidin-1-yl)-5-(isopropylamino)-3-morpholinopyrazine-2-carbonitrile

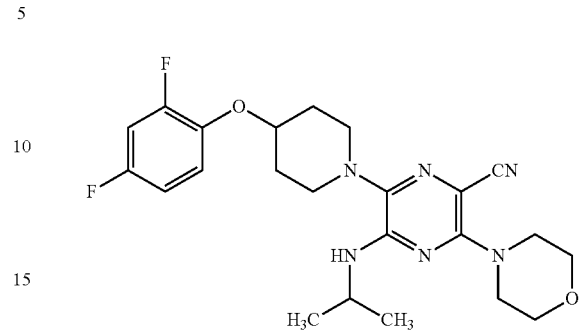

Combined 2,2'-bis(diphenylphosphino)-1,1'-binaphthalene (12.21 mg, 0.020 mmol), diacetoxypalladium (2.202 mg, 9.81 μmop, Cs2CO3 (47.9 mg, 0.147 mmol), 3-chloro-6-(4-(2,4-difluorophenoxy)piperidin-1-yl)-5-(isopropylamino)pyrazine-2-carbonitrile (20 mg, 0.049 mmol) and morpholine (8.54 mg, 0.098 mmol) in toluene (10 mL). The reaction mixture was heated in a microwave at 120° C. for 1 h. The reaction mixture was filtered and purified by HPLC using Method A to afford the title compound as its TFA salt (4 mg, 18%) as a tan film. 1H NMR (500 MHz, methanol-d4) δ ppm 1.12-1.37 (m, 6H), 1.94 (td, J=8.54, 4.39 Hz, 2H), 2.04-2.21 (m, 2H), 2.88 (ddd, J=12.33, 8.91, 3.17 Hz, 2H), 3.17-3.29 (m, 2H), 3.53-3.67 (m, 4H), 3.73-3.86 (m, 4H), 4.15-4.31 (m, 1H), 4.37-4.50 (m, 1H), 6.80-6.92 (m, 1H), 6.98 (ddd, J=11.35, 8.67, 2.93 Hz, 1H), 7.17 (td, J=9.28, 5.37 Hz, 1H); ESI-MS m/z [M+H]+ 459.4.

Example 33 6-(4-(2,4-difluorophenoxy)piperidin-1-yl)-5-(isopropylamino)-3-(methoxy methyl)pyrazine-2-carbonitrile

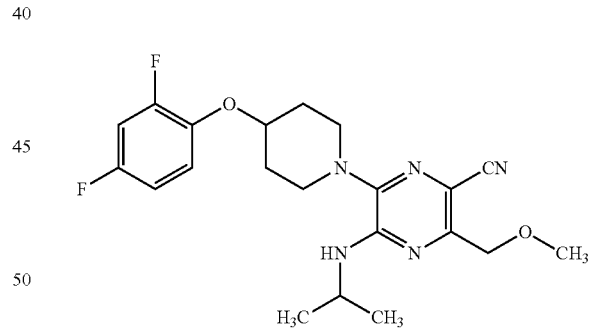

Combined 3-chloro-6-(4-(2,4-difluorophenoxy)piperidin-1-yl)-5-(isopropylamino)pyrazine-2-carbonitrile (50 mg, 0.123 mmol), PdCl2(dppf) (8.97 mg, 0.012 mmol), potassium methoxymethyltrifluoroborate (74.5 mg, 0.490 mmol) and 2N Na2CO3 (0.5 ml) in dioxane (1.0 mL). The reaction mixture was heated in a microwave at 130° C. for 30 min. The reaction mixture was filtered and purified by HPLC using Method A twice to afford the title compound as its TFA salt (6 mg, 10%) as a yellow film. 1H NMR (500 MHz, methanol-d4) ppm 1.27 (d, J=6.35 Hz, 6H) 1.87-2.04 (m, 2H) 2.08-2.20 (m, 2H) 3.05 (ddd, J=12.45, 8.54, 3.42 Hz, 2H) 3.37-3.50 (m, 2H) 4.28-4.41 (m, 1H) 4.43-4.53 (m, 3H) 6.80-6.93 (m, 1H) 6.98 (ddd, J=11.35, 8.66, 2.93 Hz, 1H) 7.17 (td, J=9.28, 5.37 Hz, 1H); ESI-MS m/z [M+H]+ 418.4.

Example 34 6-(4-(2,4-difluorobenzyl)piperazin-1-yl)-3-((2-(dimethylamino)ethoxy)methyl)-5-(isopropylamino)pyrazine-2-carbonitrile

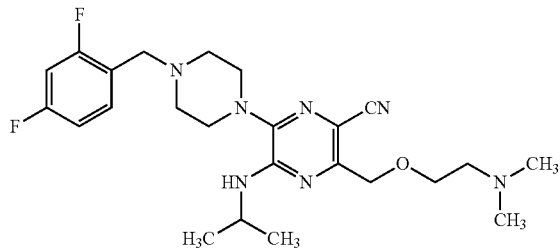 [SMILES: CC(C)Nc1nc(COCCN(C)C)c(C#N)nc1N1CCN(Cc2ccc(F)cc2F)CC1]

The title compound was prepared and purified in a manner similar to Example 33 using potassium 2-(dimethylamino)ethoxymethyltrifluoroborate in place of potassium methoxymethyltrifluoroborate. The title compound was obtained as its TFA salt (2% yield) as a clear film. 1H NMR (500 MHz, methanol-d4) δ ppm 1.26-1.29 (m, 6H), 2.94 (s, 6H), 3.24-3.46 (m, 6H), 3.67 (s, 2H), 3.95-3.97 (m, 2H), 4.38-4.39 (m, 1H), 4.47 (s, 2H), 4.65-4.68 (m, 4H), 7.12-7.30 (m, 2H), 7.67 (d, J=6.35 Hz, 1H); ESI-MS m/z [M+H]+ 474.4.

The compounds of the invention can be administered alone or in the form of a pharmaceutical composition. In practice, the compounds of the invention are usually administered in the form of pharmaceutical compositions, that is, in admixture with at least one pharmaceutically acceptable excipient. The proportion and nature of any pharmaceutically acceptable excipient(s) are determined by the properties of the selected compound of the invention, the chosen route of administration, and standard pharmaceutical practice.

In another embodiment, the present invention provides pharmaceutical compositions comprising: a compound of invention and at least one pharmaceutically acceptable excipient.

In effecting treatment of a patient in need of such treatment, a compound of the invention can be administered in any form and route which makes the compound bioavailable. The compounds of the invention can be administered by a variety of routes, including orally, in particularly by tablets and capsules. The compounds of the invention can be administered parenteral routes, more particularly by inhalation, subcutaneously, intramuscularly, intravenously, intraarterially, transdermally, intranasally, rectally, vaginally, occularly, topically, sublingually, and buccally, intraperitoneally, intraadiposally, intrathecally and via local delivery for example by catheter or stent.

One skilled in the art can readily select the proper form and route of administration depending upon the particular characteristics of the compound selected, the disorder or condition to be treated, the stage of the disorder or condition, and other relevant circumstances. The pharmaceutical compositions of the invention may be administered to the patient, for example, in the form of tablets, capsules, cachets, papers, lozenges, wafers, elixirs, ointments, transdermal patches, aerosols, inhalants, suppositories, solutions, and suspensions.

The pharmaceutical compositions of the present invention are prepared in a manner well known in the pharmaceutical art and include at least one of the compounds of the invention as the active ingredient. The amount of a compound of the present invention may be varied depending upon its particular form and may conveniently be between 1% to about 50% of the weight of the unit dose form. The term "pharmaceutically acceptable excipient" refers to those typically used in preparing pharmaceutical compositions and should be pharmaceutically pure and non-toxic in the amounts used. They generally are a solid, semisolid, or liquid material which in the aggregate can serve as a vehicle or medium for the active ingredient. Some examples of pharmaceutically acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

The present pharmaceutical compositions are preferably formulated in a unit dose form, each dose typically containing from about 0.5 mg to about 100 mg of a compounds of the invention. The term "unit dose form" refers to a physically discrete unit containing a predetermined quantity of active ingredient, in association with a suitable pharmaceutical excipient, by which one or more is used throughout the dosing regimen to produce the desired therapeutic effect. One or more "unit dose form" may be taken to affect the treatment dosage on a daily schedule.

In one particular variation, the composition is a pharmaceutical composition adapted for oral administration, such as a tablet or a capsule or a liquid formulation, for example, a solution or suspension, adapted for oral administration. In still another particular variation, the pharmaceutical composition is a liquid formulation adapted for parenteral administration.

Compounds of the present invention are modulators of GPR6, and as such are useful in the treatment and prevention of conditions associated with GPR6. As mentioned above, the major striatal targets of dopaminergic innervation reside in the medium spiny neurons (MSNs) of the striatopallidal (indirect) and striatonigral (direct) output pathways. The MSNs of the direct output pathway express D1 dopamine receptors whereas those in the indirect pathway express D2 receptors. GPR6 is enriched in D2 receptor expressing MSNs in the striatum where GPR6 activity is functionally opposed to D2 receptor signaling. Antagonism or inverse agonism of Gs coupled GPR6 decreases cAMP in MSNs and provides a functional alternative to dopamine mediated activation of D2 receptors.

Antagonism or inverse agonism of Gs coupled GPR6 provides a functional alternative to dopamine mediated activation of D2 receptors. As such, compounds that modulate the activity of GPR6 are useful for treating in a variety of neurological and psychiatric disorders. For example movement disorders including Parkinson's disease and Huntington's disease either alone or in combination with other agents are approved for the treatment of Parkinson's disease including L-DOPA, dopaminergic agonists, MAO B inhibitors, DOPA decarboxylase inhibitors and C(O)MT inhibitors. Other disease indications that could be treated by modulation of GPR6 include drug addiction and eating disorders, cognitive disorders, schizophrenia, bipolar disorders, and depression.

In another embodiment, the invention provides methods of treating conditions associated with GPR6, comprising: administering to a patient in need thereof an effective amount of a compound of the invention. In another embodiment, a compound of the invention is provided for use as a medicament. The invention also provides the use of a compound of the invention, including the use for the manufacture of a medicament, to treat the conditions associated with GPR6 described herein. The compounds of the present invention are useful as GPR6 modulators for a variety of subjects (e.g., humans, non-human mammals and non-mammals).

As used herein terms "condition," "disorder," and "disease" relate to any unhealthy or abnormal state. The term "conditions associated with GPR6" includes conditions, disorders, and diseases in which the modulators of GPR6 provides a therapeutic benefit, such as Parkinson's disease, levodopa induced dyskinesias, and Huntington's disease, drug addiction, eating disorders, cognitive disorders, schizophrenia, bipolar disorders, and depression.

The terms "treat," "treatment," and "treating" include improvement of the conditions described herein. The terms "treat," "treatment," and "treating" include all processes providing slowing, interrupting, arresting, controlling, or stopping of the state or progression of the conditions described herein, but does not necessarily indicate a total elimination of all symptoms or a cure of the condition. The terms "treat," "treatment," and "treating" are intended to include therapeutic treatment of such disorders. The terms "treat," "treatment," and "treating" are intended to include prophylactic treatment of such disorders.

As used herein the terms "patient" and "subject" includes humans and non-human animals, for example, mammals, such as mice, rats, guinea pigs, dogs, cats, rabbits, cows, horses, sheep, goats, and pigs. The term also includes birds, fish, reptiles, amphibians, and the like. It is understood that a more particular patient is a human. Also, more particular patients and subjects are non-human mammals, such as mice, rats, and dogs.

As used herein, the term "effective amount" refers to the amount of compound of the invention which treats, upon single or multiple dose administration, a patient suffering from the mentioned condition. An effective amount can be readily determined by the attending diagnostician, as one skilled in the art, by the use of known techniques and by observing results obtained under analogous circumstances. In determining the effective amount, the dose, a number of factors are considered by the attending diagnostician, including, but not limited to, the species of patient, its size, age, and general health; the specific condition, disorder, or disease involved; the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances. An effective amount of the present invention, the treatment dosage, is expected to range from 1 mg to 200 mg. Specific amounts can be determined by the skilled person. Although these dosages are based on an average human subject having a mass of about 60 kg to about 70 kg, the physician will be able to determine the appropriate dose for other patients.

The pathological hallmark of Parkinson disease (PD) is neuronal cell loss within the substantia nigra. Degeneration of the nigrostriatal pathway causes reduction in the striatal concentration of dopamine which results in motor and nonmotor clinical manifestations. Many Parkinson's disease patients are treated with levodopa, a prodrug for dopamine. Levodopa has common serious side effects including induced dyskinesia (LID), impulsive control disorders (ICD), psychotic symptoms and sleep disturbances. LID is progressive (90% of PD patients develop LID within 10 yrs). Irreversible adaptations occur in D1 receptor signaling in MSNs in rodent models of LID including reduced desensitization leading to hypersensitivity in the direct pathway. Genetic inactivation of D1 but not D2 receptors abolishes LID in mice. However blockade of D1 receptor signaling does not affect the antiparkinsonian efficacy of L-DOPA.

In a particular embodiment, the present invention provides a method of treating Parkinson's disease comprising: administering to a patient in need thereof an effective amount of a compound of the invention. That is, the invention also provides the use of a compound of the invention, including the use for the manufacture of a medicament, to treat Parkinson's disease.

The compounds of the invention may be combined with one or more other pharmacologically active compounds or therapies for the treatment of one or more disorders, diseases or conditions for which GPR6 is indicated may be administered simultaneously, sequentially or separately in combination with one or more compounds or therapies for treating Parkinson's disease, levodopa induced dyskinesias, and Huntington's disease, drug addiction, eating disorders, cognitive disorders, schizophrenia, bipolar disorders, and depression. Such combinations may offer significant therapeutic advantages, including fewer side effects, improved ability to treat underserved patient populations, or synergistic activity. In particular, the compounds of the invention may be administered with levodopa for treating Parkinson's disease. The present invention provides a method treating Parkinson's disease comprising: administering to a patient in need thereof an effective amount of a compound of the invention in combination with levadopa. The invention also provides the use of a compound of the invention in combination with levadopa, including the use for the manufacture of a medicament, to treat Parkinson's disease.

The activity of compounds as GPR6 modulators may be determined by a variety of methods, including in vitro and in vivo methods.

Example A.1

Inhibition of cAMP Activity of GPR6 In Vitro Assay

This cell based assay measures the ability of compounds to inhibit the constitutive cAMP activity of GPR6 receptor expressed in CHO-K1 cells. CHO cells were stably expressed with GPR6 receptor, whose expression is controlled by a tetracycline inducible element. The cells were cultured in medium containing F12K, 10% FBS, 1% Penn/Strep, 200 ug/mL Hygromycin. GPR6 receptor expression was induced for 20 hrs with 10 g/ml doxycycline (sigma D9891) in growth media. After addition of doxycycline cells were plated at a density of 250-500 cells per well in half-volume black clear bottom plates (Costar) and place in an incubator (37°, 5% C(O)2) for 20 hours prior to cAMP assays.

Culture media was removed from cells and they were washed with 50 L of Ringer's Buffer (MgCl2 0.047 mg/mL, NaH2PO4 0.18 mg/mL, Na2HPO4 0.1 mg/mL, KCl 0.34 mg/mL, NaHC(O)3 1.26 mg/mL, D-glucose 1.8 mg/mL, NaCl 7 mg/mL; pH=7.4). Compounds suspended in DMSO were diluted in Ringer's Buffer containing 0.5% fatty acid free BSA and incubated on cells for 45 min at 37° and 5% C(O)2. After incubation cells were incubated for 10 min at room temp with Eu-cAMP tracer solution from a Perkin Elmer Lance HTRF UltracAMP assay kit (TRF0264). Then ULight™-anti-cAMP solution from the Lance HTRF kit was added and incubated on a shaker at room temp for 1 hour prior to HTRF detection in a BMG PolarStar Omega.

IC50 curves were generated with a four-parameter logistic equation using GraphPad Prism 5.03. Measured IC50 value (µM) of example compounds in this assay is provided in the table below.

Example A.2

Inhibition of cAMP Activity of GPR6 In Vitro Assay

This cell based assay measures the ability of compounds to inhibit the constitutive cAMP activity of GPR6 receptor expressed in CHO-K1 cells. CHO cells were stably expressed with GPR6 receptor, whose expression is controlled by a tetracycline inducible element. The cells were cultured in medium containing F12K, 10% FBS, 1% Penn/Strep, 200 ug/mL Hygromycin. GPR6 receptor expression was induced for 20 hrs with 2 □g/ml doxycycline (sigma D9891) in growth media. After addition of doxycycline cells were plated at a density of 450-750 cells per well in 96-well half-volume black tissue culture plates (Costar) and placed in an incubator (37°, 5% CO2) for 20 hours prior to cAMP assays.

Culture media was removed from cells and they were washed with 50 L/well of Ringer's Buffer (MgCl2 0.047 mg/mL, NaH2PO4 0.18 mg/mL, Na2HPO4 0.1 mg/mL, KCl 0.34 mg/mL, NaHCO3 1.26 mg/mL, D-glucose 1.8 mg/mL, NaCl 7 mg/mL; pH=7.4). Compounds suspended in DMSO were diluted in Ringer's Buffer containing 0.5% fatty acid free BSA plus 300 µM IBMX and incubated on cells for 45 min at 37° and 5% CO2. After incubation cells were incubated for 10 min at room temp with Eu-cAMP tracer solution from a Perkin Elmer Lance HTRF Ultra cAMP assay kit (TRF0263). Then ULight™-anti-cAMP solution from the Lance HTRF kit was added and incubated on a shaker at room temp for 1 hour prior to HTRF detection in a Perkin Elmer Envision plate reader.

EC50 curves were generated with a four-parameter logistic equation using GraphPad Prism 5.03. Measured EC50 value (µM) of example compounds in this assay is provided nM in the Table 1 below.

TABLE 1

| Ex. | A. 1 EC50 | A. 2 EC50 |
|---|---|---|
| 1 | | |
| 2 | | |
| 3 | | |
| 4 | | |
| 5 | | 32.7 |
| 6 | | |
| 7 | | |
| 8 | | |
| 9 | | |
| 10 | | |
| 11 | | |
| 12 | | |
| 13 | | 49.3 |
| 14 | | 38.7 |
| 15 | | 36.9 |
| 16 | | 123 |
| 17 | | 23 |
| 18 | | 6.8 |
| 19 | 50.5 | |
| 20 | | |
| 21 | | 50.3 |
| 22 | | 30.2 |
| 23 | | 172 |
| 24 | | 48.2 |
| 25 | | 242 |

TABLE 1-continued

| Ex. | A. 1 EC50 | A. 2 EC50 |
|---|---|---|
| 26 | | 72.3 |
| 27 | | 161 |
| 28 | | 77 |
| 29 | | 184 |
| 30 | | 30.2 |
| 31 | | 18.0 |
| 32 | | 23.5 |
| 33 | | 13.7 |
| 34 | | 62.5 |

Example B

Haloperidol-Induced Catalepsy—In Vivo Rodent Parkinson's Disease Model

The motor symptoms of Parkinson's disease include akinesia, bradykinesia, rigidity, tremor and postural abnormalities and are associated with the loss of nigral dopaminergic cells and a decline in striatal dopamine levels. Administration of haloperidol to rodents leads to a transient parkinsonian-like state that is reversed by the administration of L-Dopa (Duty, S.; Jenner, P. Br. J. Pharmacol. (2011), 164, 1357-1391) and other drugs that have been clinically validated for the treatment of Parkinson's disease. Haloperidol antagonizes dopamine D2 and, to a lesser extent, D1 receptors in medium spiny neurons that comprise the indirect and direct pathways of the motor circuit respectively. The resultant block of striatal dopamine transmission results in abnormal downstream firing within the basal ganglia circuits that is manifest as symptoms of muscle rigidity and catalepsy. Catalepsy has been postulated to reflect the clinical features of Parkinson's disease, whereby patients experience an inability of to initiate movements.

Male Sprague-Dawley rats (Charles River, Calco, Italy) weighing 175-200 g are used. Alternatively, male C57B16 mice weighing 25-35 g were used. The cataleptic state was induced by the subcutaneous administration of the dopamine receptor antagonist haloperidol (0.3 mg/kg, sc), 90 min before testing the animals on the vertical grid test. For this test, the rats or mice were placed on the wire mesh cover of a 25 cm×43 cm plexiglass cage placed at an angle of about 70 degrees with the bench table. The subject was placed on the grid with all four legs abducted and extended ("frog posture"). The use of such an unnatural posture is essential for the specificity of this test for catalepsy. The time span from placement of the paws until the first complete removal of one paw (descent latency) was measured maximally for 120 sec for rats. For mice, the front paws of a mouse was placed on a horizontal metal bar raised 2" above a Plexiglas platform and time was recorded for up to 30 seconds per trial. The test ended when the animal's front paws returned to the platform or after 30 seconds. The test was repeated three times and the average of the three trials was reported as the intensity index of catalepsy.

Catalepsy was measured 30 min, 120 min, and/or 240 min after dosing the subjects a 0.3 mg/kg i.p. dose of haloperidol along with the GPR6 modulator test compound. Test compound plasma and brain levels were determined by collected tissue samples at the end of the experiment, which was either at the 120 or 240 min time point. A representative number of compounds of the invention were administered in a dose range from 0.1 to 100 mg/kg i.p, sc or po in conjunction with haloperidol. The A2a antagonist KW6002 (istradefylline) was dosed at 0.6 mg/kg i.p. as a positive control.

What is claimed is:
1. The compound of formula I

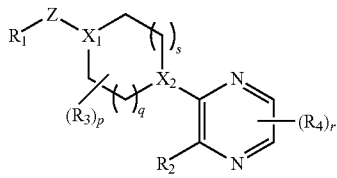

or a pharmaceutically acceptable salt thereof, wherein
$R_1$ is selected from the group consisting of optionally substituted $C_{3-8}$ cycloalkyl, optionally substituted $C_{3-6}$ heterocyclyl, optionally substituted $C_{6-10}$ aryl, and optionally substituted $C_{1-10}$ heteroaryl;
$X_1$ is N and $X_2$ is CH; or
$X_1$ is CH and $X_2$ is N; or
$X_1$ is N and $X_2$ is N;
when $X_1$ is N, Z is selected from the group consisting of $C_{1-6}$ alkylene, $C_{1-6}$ haloalkylene, —C(O)—, and —S(O)$_2$—;
when $X_1$ is CH, Z is selected from the group consisting of $C_{1-6}$ alkylene, $C_{1-6}$ haloalkylene, —O—, —C(O)—, —NH—, —S—, —S(O)—, and —S(O)$_2$—;
q is 0, 1, or 2;
s is 0, 1, or 2;
$R_2$ is —OR$_5$ or —NR$_6$R$_7$;
$R_3$, each time taken, is independently selected from the group consisting of $C_{1-6}$ alkyl, $C_{3-8}$ cycloalkyl, and trifluoromethyl;
p is 0, 1, or 2;
$R_4$, each time taken, is independently selected from the group consisting of $C_{1-6}$ alkyl, cyano, hydroxy, halo, optionally substituted $C_{3-6}$ heterocyclyl, —C(O)—R$_8$, —C(O)—N(R$_9$)(R$_{10}$), and —C(O)—OR$_{11}$;
r is 1 or 2;
$R_5$ is selected from the group consisting of $C_{1-6}$ alkyl and $C_{3-8}$ cycloalkyl;
$R_6$ is selected from the group consisting of hydrogen and $C_{1-6}$ alkyl;
$R_7$ is selected from the group consisting of optionally substituted $C_{1-6}$ alkyl, $C_{3-8}$ cycloalkyl, optionally substituted $C_{6-10}$ aryl, optionally substituted $C_{1-10}$ heteroaryl, and optionally substituted $C_{3-6}$ heterocyclyl;
$R_8$ is selected from the group consisting of optionally substituted $C_{1-6}$ alkyl, $C_{3-8}$ cycloalkyl, optionally substituted $C_{6-10}$ aryl, optionally substituted $C_{1-10}$ heteroaryl, and optionally substituted $C_{3-6}$ heterocyclyl;
$R_9$ is selected from the group consisting of hydrogen and optionally substituted $C_{1-6}$ alkyl;
$R_{10}$ is selected from the group consisting of hydrogen, $C_{1-6}$ alkyl and $C_{3-8}$ cycloalkyl; or
$R_9$ and $R_{10}$ are taken together with the nitrogen to which they are attached form a 4 to 7 membered, saturated, ring optionally having 1 additional ring heteroatom selected from the group N, O, and S and optionally substituted on any of the ring carbon atoms with 1 to 5 substituents independently selected from the group consisting of cyano, halo, hydroxy, amino, optionally substituted $C_{3-6}$ heterocyclyl, $C_{1-9}$ amide, optionally substituted $C_{1-6}$ alkyl, and $C_{1-4}$ alkoxy and substituted on any additional ring nitrogen by a substituent selected from the group consisting of hydrogen, $C_{3-8}$ cycloalkyl, and optionally substituted $C_{1-6}$ alkyl; and $R^{11}$ is selected from the group consisting of hydrogen and $C_{3-8}$ cycloalkyl.

2. The compound or pharmaceutically acceptable salt thereof according to claim 1, wherein $X_1$ is CH and $X_2$ is N.
3. The compound or pharmaceutically acceptable salt thereof according to claim 1, wherein $X_1$ is N and $X_2$ is N.
4. The compound or pharmaceutically acceptable salt thereof according to claim 3, wherein an $R_4$ is cyano.
5. The compound or pharmaceutically acceptable salt thereof according to claim 1, wherein $R_1$ is optionally substituted $C_{6-10}$ aryl or a pharmaceutically acceptable salt thereof.
6. The compound or pharmaceutically acceptable salt thereof according to claim 1, wherein Z is $C_{1-6}$ alkylene.
7. The compound or pharmaceutically acceptable salt thereof according to claim 1, wherein Z is —O—.
8. The compound or pharmaceutically acceptable salt thereof according to claim 1, wherein Z is —C(O)—.
9. The compound or pharmaceutically acceptable salt thereof according to claim 1, wherein $R_2$ is —NR$_6$R$_7$.
10. A compound, which is selected from the group consisting of:
(R)-3-cyano-5-(4-((2,4-difluorophenyl)fluoromethyl)piperidin-1-yl)-N-(2-(dimethylamino)ethyl)-6-(isopropylamino)-N-methylpyrazine-2-carboxamide;
6-(4-(2,4-difluorophenoxy)piperidin-1-yl)-N-(2-(dimethylamino)-ethyl)-5-(isopropylamino)-N-methylpyrazine-2-carboxamide; and
6-(4-(2,4-difluorophenoxy)piperidin-1-yl)-5-(isopropylamino)-3-(methoxymethyl)pyrazine-2-carbonitrile; and
6-(4-(2,4-difluorobenzyl)piperazin-1-yl)-3-((2-(dimethylamino)ethoxy)methyl)-5-(isopropylamino)pyrazine-2-carbonitrile;
or a pharmaceutically acceptable salt of any one of the above-mentioned compounds.

11. A pharmaceutical composition comprising a compound or pharmaceutically acceptable salt thereof as defined in claim 1, and a pharmaceutically acceptable excipient.

12. A method of treating a disease, disorder or condition in a subject, the method comprising administering to the subject a compound of formula I

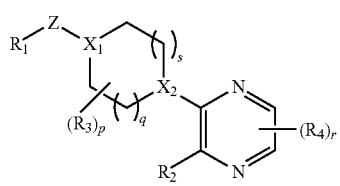

or pharmaceutically acceptable salt thereof, wherein
$R_1$ is selected from the group consisting of optionally substituted $C_{3-8}$ cycloalkyl, optionally substituted $C_{3-6}$ heterocyclyl, optionally substituted $C_{6-10}$ aryl, and optionally substituted $C_{1-10}$ heteroaryl;
$X_1$ is N and $X_2$ is CH; or
$X_1$ is CH and $X_2$ is N; or
$X_1$ is N and $X_2$ is N;
when $X_1$ is N, Z is selected from the group consisting of $C_{1-6}$ alkylene, $C_{1-6}$ haloalkylene, —C(O)—, and —S(O)$_2$—;
when $X_1$ is CH, Z is selected from the group consisting of $C_{1-6}$ alkylene, $C_{1-6}$ haloalkylene, —O—, —C(O)—, —NH—, —S—, —S(O)—, and —S(O)$_2$—;

q is 0, 1, or 2;

s is 0, 1, or 2;

$R_2$ is —$OR_5$ or —$NR_6R_7$;

$R_3$, each time taken, is independently selected from the group consisting of $C_{1-6}$ alkyl, $C_{3-8}$ cycloalkyl, and trifluoromethyl;

p is 0, 1, or 2;

$R_4$, each time taken, is independently selected from the group consisting of optionally substituted $C_{1-6}$ alkyl, cyano, hydroxy, halo, optionally substituted $C_{3-6}$ heterocyclyl, —C(O)—$R_8$, —C(O)—N($R_9$)($R_{10}$), and —C(O)—$OR_{11}$;

r is 1 or 2;

$R_5$ is selected from the group consisting of $C_{1-6}$ alkyl and $C_{3-8}$ cycloalkyl;

$R_6$ is selected from the group consisting of hydrogen and $C_{1-6}$ alkyl;

$R_7$ is selected from the group consisting of optionally substituted $C_{1-6}$ alkyl, $C_{3-8}$ cycloalkyl, optionally substituted $C_{6-10}$ aryl, optionally substituted $C_{1-10}$ heteroaryl, and optionally substituted $C_{3-6}$ heterocyclyl;

$R_8$ is selected from the group consisting of hydrogen, optionally substituted $C_{1-6}$ alkyl, $C_{3-8}$ cycloalkyl, optionally substituted $C_{6-10}$ aryl, optionally substituted $C_{1-10}$ heteroaryl, and optionally substituted $C_{3-6}$ heterocyclyl;

$R_9$ is selected from the group consisting of hydrogen and optionally substituted $C_{1-6}$ alkyl;

$R_{10}$ is selected from the group consisting of hydrogen, $C_{1-6}$ alkyl and $C_{3-8}$ cycloalkyl; or $R_9$ and $R_{10}$ are taken together with the nitrogen to which they are attached form a 4 to 7 membered, saturated, ring optionally having 1 additional ring heteroatom selected from the group N, O, and S and optionally substituted on any of the ring carbon atoms with 1 to 5 substituents independently selected from the group consisting of cyano, halo, hydroxy, amino, optionally substituted $C_{3-6}$ heterocyclyl, $C_{1-9}$ amide, optionally substituted $C_{1-6}$ alkyl, and $C_{1-4}$ alkoxy and substituted on any additional ring nitrogen by a substituent selected from the group consisting of hydrogen, $C_{3-8}$ cycloalkyl, and optionally substituted $C_{1-6}$ alkyl; and $R_{11}$ is selected from the group consisting of hydrogen, $C_{1-6}$ alkyl, and $C_{3-8}$ cycloalkyl;

wherein the disease, disorder or condition is selected from Parkinson's disease, levodopa induced dyskinesias, Huntington's disease, drug addiction, eating disorders, cognitive disorders, schizophrenia, bipolar disorders, and depression.

* * * * *